US011406720B2

(12) United States Patent
Wang et al.

(10) Patent No.: US 11,406,720 B2
(45) Date of Patent: Aug. 9, 2022

(54) FIBROBLAST GROWTH FACTOR RECEPTOR 2-SPECIFIC PEPTIDE REAGENTS AND METHODS

(71) Applicant: THE REGENTS OF THE UNIVERSITY OF MICHIGAN, Ann Arbor, MI (US)

(72) Inventors: Thomas D. Wang, Ann Arbor, MI (US); Juan Zhou, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 114 days.

(21) Appl. No.: 16/625,054

(22) PCT Filed: Jun. 20, 2018

(86) PCT No.: PCT/US2018/038553
§ 371 (c)(1),
(2) Date: Dec. 20, 2019

(87) PCT Pub. No.: WO2018/237041
PCT Pub. Date: Dec. 27, 2018

(65) Prior Publication Data
US 2020/0138979 A1 May 7, 2020

Related U.S. Application Data

(60) Provisional application No. 62/523,446, filed on Jun. 22, 2017.

(51) Int. Cl.
*A61K 49/00* (2006.01)
*C07K 1/13* (2006.01)
*C07K 7/08* (2006.01)

(52) U.S. Cl.
CPC ...... *A61K 49/0032* (2013.01); *A61K 49/0041* (2013.01); *A61K 49/0056* (2013.01); *C07K 1/13* (2013.01); *C07K 7/08* (2013.01)

(58) Field of Classification Search
CPC .. A61K 2123/00; A61K 2121/00; A61K 9/00; A61K 9/5169; A61K 9/1075; A61K 47/42; A61K 49/00; A61K 49/0032; A61K 49/0041; A61K 49/0056; A61K 49/221; A61K 49/14; A61K 51/00; A61K 51/08; A61K 31/00; A61K 31/555; A61K 31/337; A61K 31/513; A61K 31/7068; A61K 31/44; A61K 31/4745; A61K 31/196; A61K 33/00; A61K 33/243; C07K 1/13; C07K 7/08; A61P 35/00; A61P 35/04
USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.5, 514/21.8; 530/300
See application file for complete search history.

(56) References Cited

U.S. PATENT DOCUMENTS

2009/0042802 A1   2/2009  Pan et al.
2010/0111944 A1   5/2010  Pollock et al.
2011/0059091 A1   3/2011  Chang et al.

FOREIGN PATENT DOCUMENTS

CN      102453079 A       5/2012
WO    WO-01/55339 A2      8/2001
WO   WO-2015/104314 A1    7/2015

OTHER PUBLICATIONS

Bai et al., "GP369, an FGFR2-IIIb-specific antibody, exhibits potent antitumor activity against human cancers driven by activated FGFR2 signaling," Cancer Res 70:7630-9 (2010).
Bi et al., "One-step synthesis of peptide conjugated gold nanoclusters for the high expression of FGFR2 tumor targeting and imaging," RSC Adv 6:4627-33 (2016).
Bird-Lieberman et al., "Molecular imaging using fluorescent lectins permits rapid endoscopic identification of dysplasia in Barrett's esophagus," Nat Med 18:315-21 (2012).
Boonstra et al., "Verification and unmasking of widely used human esophageal adenocarcinoma cell lines," J Natl Cancer Inst 102:271-4 (2010).
Curvers et al., "Low-grade dysplasia in Barrett's esophagus: overdiagnosed and underestimated," Am J Gastroenterol 105:1523-30 (2010).
Cwirla et al., "Peptides on phage: A vast library of peptides for identifying ligands," Proc. Natl. Acad. Sci. USA, 87:6378-6382 (1990).
Dufour et al., "FGFR2-Cbl interaction in lipid rafts triggers attenuation of PI3K/Akt signaling and osteoblast survival," Bone 42:1032-9 (2008).
Dulak et al., "Exome and whole-genome sequencing of esophageal adenocarcinoma identifies recurrent driver events and mutational complexity," Nat Genet 45:478-86 (2013).
Eswarakumar et al., "Cellular signaling by fibroblast growth factor receptors," Cytokine Growth Factor Rev 16:139-49 (2005).
Fang et al., "SNORD126 promotes HCC and CRC cell growth by activating the PI3K-AKT pathway through FGFR2," J Mol Cell Biol 9(3):243-255 (2017).
Fletcher et al., "Master regulators of FGFR2 signalling and breast cancer risk," Nat Commun 4:2464-1-12 (2013).
Giacchino et al., "Clinical utility and interobserver agreement of autofluorescence imaging and magnification narrow-band imaging for the evaluation of Barrett's esophagus: a prospective tandem study," Gastrointest Endosc 77:711-8 (2013).

(Continued)

*Primary Examiner* — D. L. Jones
(74) *Attorney, Agent, or Firm* — Marshall, Gerstein & Borun LLP

(57) ABSTRACT

The present disclosure relates to Fibroblast Growth Factor Receptor 2-specific peptide reagents, methods for detecting epithelial-derived cancer cells such as esophageal, colorectal, gastric, pancreatic or breast carcinoma cells using the peptide reagents, and methods for targeting such cells using the peptide reagents.

21 Claims, 19 Drawing Sheets

Specification includes a Sequence Listing.

(56) References Cited

OTHER PUBLICATIONS

Han et al., "Evaluation of Fibroblast Growth Factor Receptor 2 Expression, Heterogeneity and Clinical Significance in Gastric Cancer," Pathobiology 82:269-79 (2015).
Hur et al., "Trends in esophageal adenocarcinoma incidence and mortality," Cancer 119:1149-58 (2013).
Ibrahimi et al., "Structural basis for fibroblast growth factor receptor 2 activation in Apert syndrome," Proc Natl Acad Sci 98:7182-7 (2001).
International Search Report and Written Opinion from International Application No. PCT/US18/38553 dated Sep. 20, 2018.
Joshi et al., "Design and Synthesis of Near-Infrared Peptide for in Vivo Molecular Imaging of HER2," Bioconjug Chem 27:481-94 (2016).
Joshi et al., "Multimodal endoscope can quantify wide-field fluorescence detection of Barrett's neoplasia," Endoscopy 48:A1-A13 (2016).
Joshi et al., "Multispectral endoscopic imaging of colorectal dysplasia in vivo," Gastroenterology 143:1435-7 (2012).
Joshi et al., "Near-infrared-labeled peptide multimer functions as phage-mimic for high affinity, specific targeting of colonic adenomas in vivo," Gastrointestinal Endoscopy 76(6):1197-206 (2012).
Kato et al., "Gene amplification of EGFR, HER2, FGFR2 and MET in esophageal squamous cell carcinoma," Int J Oncol 42:1151-8 (2013).
Khondee et al., "Targeted therapy of colorectal neoplasia with rapamycin in peptide-labeled pegylated octadecyl lithocholate micelles," J. Controlled Release 199:114-121 (2015).
Kim et al., "Pazopanib, a novel multitargeted kinase inhibitor, shows potent in vitro antitumor activity in gastric cancer cell lines with FGFR2 amplification," Mol Cancer Ther 13:2527-36 (2014).
Lee et al., "Low prognostic implication of fibroblast growth factor family activation in triple-negative breast cancer subsets," Ann Surg Oncol 21:1561-8 (2014).
Luo et al., "A review of NIR dyes in cancer targeting and imaging," Biomaterials 32:7127-38 (2011).
Macindoe et al., "HexServer: an FFT-based protein docking server powered by graphics processors," Nucleic Acids Research, 38(S2):W445-W449 (2010).
Mannath et al., "Narrow band imaging for characterization of high grade dysplasia and specialized intestinal metaplasia in Barrett's esophagus: a meta-analysis," Endoscopy 42:351-9 (2010).
Matsuda et al., "Fibroblast growth factor receptor 2: expression, roles, and potential as a novel molecular target for colorectal cancer," Patholog Res Int 2012:574768, 8 pages (2012).
Matsuda et al., "Inhibition of fibroblast growth factor receptor 2 attenuates proliferation and invasion of pancreatic cancer," Cancer Sci 105:1212-9 (2014).
Merrifield, "Solid Phase Peptide Synthesis. I. The Synthesis of a Tetrapeptide," J Am Chem Soc 85:2149-2154 (1963).
Ngamruengphong et al., "Diagnostic yield of methylene blue chromoendoscopy for detecting specialized intestinal metaplasia and dysplasia in Barrett's esophagus: a meta-analysis," Gastrointest Endosc 69:1021-8 (2009).
Nomura et al., "FGF10/FGFR2 signal induces cell migration and invasion in pancreatic cancer," Br J Cancer 99(2):305-13 (2008).
Odze, "Diagnosis and grading of dysplasia in Barrett's oesophagus," J Clin Pathol 59:1029-38 (2006).
Ornitz et al., "The Fibroblast Growth Factor signaling pathway," WIREs Dev Biol 4:215-66 (2015).
Orr-Urtreger et al., "Developmental localization of the splicing alternatives of fibroblast growth factor receptor-2 (FGFR2)," Dev Biol 158:475-86 (1993).
Pasqualini et al., "Organ targeting in vivo using phage display peptide libraries," Nature, 380:364-366 (1996).
Paterson et al., "Characterization of the timing and prevalence of receptor tyrosine kinase expression changes in oesophageal carcinogenesis," J Pathol 230:118-28 (2013).
Plotnikov et al., "Crystal structures of two FGF-FGFR complexes reveal the determinants of ligand-receptor specificity.," Cell 101:413-24 (2000).
Scott et al., "Identification of the amino acids comprising a surface-exposed epitope within the nucleotide-binding domain of the $NA^+$, $K^+$-ATPase using a random peptide library," Science 249:386-390(1990).
Sergina et al., "Escape from HER-family tyrosine kinase inhibitor therapy by the kinase-inactive HER3," Nature 445:437-41 (2007).
Sharma et al., "The American Society for Gastrointestinal Endoscopy PIVI (Preservation and Incorporation of Valuable Endoscopic Innovations) on imaging in Barrett's Esophagus," Gastrointest Endosc 76:252-4 (2012).
Sturm et al., "Emerging optical methods for surveillance of Barrett's oesophagus," Gut 64(11):1816-23 (2015).
Sturm et al., "In vivo molecular imaging of Barrett's esophagus with confocal laser endomicroscopy," Gastroenterology 145:56-8 (2013).
Sturm et al., "Targeted imaging of esophageal neoplasia with a fluorescently labeled peptide: first-in-human results," Sci Transl Med 5(184), 19 pages (2013).
Svensson et al., "Crystal Structure of N-Glycosylated Human Glypican-1 Core Protein," J Biol Chem, 287:14040-14051 (2012).
Thomas et al., "In vitro binding evaluation of 177Lu-AMBA, a novel 177Lu-labeled GRP-R agonist for systemic radiotherapy in human tissues," Clin Exp Metastasis. 26:105-19 (2009).
Tokunaga et al., "Fibroblast growth factor receptor 2 expression, but not its genetic amplification, is associated with tumor growth and worse survival in esophagogastric junction adenocarcinoma," Oncotarget 7:19748-61 (2016).
Torre et al., "Global Cancer Incidence and Mortality Rates and Trends—An Update," Cancer Epidemiol Biomarkers Prev 25:16-27 (2016).
UniProtKB accession No. Q63767 [online] retrieved from https://www.uniprot.org/uniprot/Q63767 (2000).
Wang et al., "Updated guidelines 2008 for the diagnosis, surveillance and therapy of Barrett's esophagus," Am J Gastroenterol 103:788-97 (2008).
Whiteman et al., "Combined effects of obesity, acid reflux and smoking on the risk of adenocarcinomas of the oesophagus," Gut 57:173-80 (2008).
Wu et al., "Arming antibodies: prospects and challenges for immunoconjugates," Nat Biotechnol 23:1137-46 (2005).
Zhang et al., "Self-Asembled Lipid-Polymer Hybrid Nanoparticles: A Robust Drug Delivery Platform," ACS NANO, 2(8):1696-1709 (2008).
Zhong et al., "Ligand-Directed Active Tumor-Targeting Polymeric Nanoparticles for Cancer Chemotherapy," Biomacromolecules, 15:1955-1969 (2014).
Zhou et al., "EGFR Overexpressed in Colonic Neoplasia Can be Detected on Wide-Field Endoscopic Imaging," Clin Transl Gastroenterol. 6:e101, 11 pages (2015).
Zhou et al., "Identification and validation of FGFR2 peptide for detection of early Barrett's neoplasic," Oncotarget 8(50):87095-87106 (2017).

FIBROBLAST GROWTH FACTOR RECEPTOR 2-SPECIFIC PEPTIDE REAGENTS AND METHODS

This is a U.S. National Phase of International Application No. PCT/US2018/038553, filed Jun. 20, 2018, which claims priority to U.S. Provisional Patent Application No. 62/523,446 filed on Jun. 22, 2017, which is incorporated herein by reference in its entirety.

STATEMENT OF GOVERNMENT SUPPORT

This invention was made with government support under Grant Nos. U54 CA163059 and U01 CA189291 awarded by the National Institute of Health. The government has certain rights in the invention.

INCORPORATION BY REFERENCE OF THE SEQUENCE LISTING

This application contains, as a separate part of disclosure, a Sequence Listing in computer-readable form (filename: 52083PCT_SeqListing.txt; 1,080 bytes—ASCII text file created: Jun. 20, 2018) which is incorporated by reference herein in its entirety.

FIELD OF THE INVENTION

The present disclosure relates to Fibroblast Growth Factor Receptor 2 (FGFR2)-specific peptide reagents, methods for detecting epithelial-derived cancer cells such as esophageal, colorectal, gastric, pancreatic or breast carcinoma cells using the peptide reagents, and methods for targeting such cells using the peptide reagents.

BACKGROUND

There are over 450,000 new cases of esophageal cancer diagnosed worldwide each year, resulting in more than 400,000 deaths annually.[1] Esophageal adenocarcinoma (EAC) represents the majority of cases in the U.S., where incidence and mortality continue to rise rapidly.[2] This trend is attributed to increasing obesity and chronic gastroesophageal reflux disease (GERD).[3] Barrett's esophagus (BE) is a replacement of normal squamous epithelium with intestinal metaplasia, and can transform into low-grade dysplasia (LGD) and progress to high-grade dysplasia (HGD) prior to development of EAC.[4] LGD represents increased risk, but pathological diagnosis of this condition can be subjective and inconsistent in interpretation.[5] Conventional white light endoscopy with random four-quadrant tissue biopsies has been recommended for surveillance of BE patients.[6] Therapy includes endoscopic mucosal resection (EMR), radio-frequency ablation (RFA), and surgery for improved patient outcomes.[6] Unfortunately, endoscopic strategies for detection of pre-malignant lesions are limited by sampling error, flat architecture, and patchy distribution.[7] Molecular changes associated with gene alterations precede histopathological abnormalities, and may be developed for imaging as an adjunct to endoscopy for early cancer detection.[8]

Receptor tyrosine kinases (RTKs) are expressed on the cell membrane, where they are accessible for in vivo imaging.[9] They occupy key regulation points for cell signaling during cancer progression. FGFR2 has been found to be highly expressed early in progression from BE to EAC.[10] FGFR2 is a member of the fibroblast growth factor receptor (FGFR) family that includes FGFR1-4,[11] which are glycoproteins located on the cell surface, and consist of 3 extracellular immunoglobulin (Ig)-like domains, a hydrophobic transmembrane region, and a cytoplasmic domain that contains a tyrosine kinase catalytic domain.[12] More than 20 alternative splicing variants of FGFR2 have been identified.[13] Major splicing occurs in the carboxyl terminus of the third Ig-like domain (D3). Isoform IIIb or IIIc of FGFR2 is generated when the C-terminus of D3 is encoded by either exon 8 or 9, respectively. FGF-1,3,7,10, and 22 are known to bind to FGFR2b, while FGF-1,2,4,6,9,17, and 18 bind to FGFR2c. Binding of FGF to FGFR2 phosphorylates specific tyrosine residues that mediate interactions with cytosolic adaptor proteins and activates intracellular signaling cascades, such as RAS-MAPK, PI3K-AKT, PLCγ, and STAT.[14-18]

Use of peptides to detect and localize Barrett's neoplasia with imaging has recently been demonstrated in the clinic.[19,20] One peptide ASYNYDA (SEQ ID NO: 4) was selected using phage display in an unbiased screen against human H460 adenocarcinoma cells and was found later to be lung rather than esophageal in origin.[26]

A peptide specific for FGFR2 was developed as a precursor for red luminescent gold nanoclusters.[30]

Probes that target FGFR2, including antibodies, lectins, and small molecules, are being developed. GP369 is an antibody specific for FGFR2b that exhibits potent anti-tumor activity.[31] Antibodies have been repurposed for in vivo imaging, however widespread clinical use of this probe platform for diagnostics has been limited by slow binding kinetics, immunogenicity, and high production costs.[32] Lectins have been shown to target Barrett's neoplasia ex vivo.[33] However, these agents have low diversity and may not achieve sufficient binding affinity for in vivo use. Moreover, the glycoprotein targets are under expressed with progression of disease, thus produce a negative contrast that can be prone to false-positives in vivo. Tyrosine kinase inhibitors have been shown to decrease survival of gastric cancer cells with FGFR2 amplifications in vitro.[34] Other methods of wide-area endoscopy, including chromoendoscopy,[35] narrowband imaging (NBI),[36] and autofluorescence imaging (AFI),[37] have been evaluated clinically, but provide low intrinsic contrast and are based on non-specific mechanisms. In clinical studies, these approaches have not demonstrated a clear advantage over conventional white light endoscopy with random biopsies.

New products and methods for detection and treatment of epithelial-derived cancers such as Barrett's neoplasia are needed in the art.

SUMMARY

In one aspect, the disclosure provides a reagent comprising a peptide SRRPASFRTARE (SEQ ID NO: 1), or a multimer form of the peptide, wherein the reagents specifically bind to FGFR2. In some embodiments, the multimer form is a dimer. In some embodiments the peptide reagent consists essentially of the peptide or multimer form of the peptide.

In some embodiments, the reagent comprises at least one detectable label attached to the peptide or multimer form of the peptide. In some embodiments, the detectable label is detectable by optical, photoacoustic, ultrasound, positron emission tomography (PET) or magnetic resonance imaging. In some embodiments, the label detectable by optical imaging is fluorescein isothiocyanate (FITC), Cy5, Cy5.5, or IRdye800. In some embodiments, the detectable label is attached to the peptide by a peptide linker. In some embodiments, the terminal amino acid of the linker is lysine. In some embodiment, the linker comprises the sequence GGGSK set out in SEQ ID NO: 2.

In some embodiments, the reagent comprises at least one therapeutic moiety attached to the peptide or multimer form of the peptide. In some embodiments, the therapeutic moiety is a chemopreventative or chemotherapeutic agent such as celecoxib, carboplatin, paclitaxel, cisplatin, 5-fluorouracil (5-FU), oxaliplatin, capecitabine, chlorambucil, sorabenib and irinotecan. In some embodiments, the therapeutic moiety is a nanoparticle or micelle, such as a polymeric nanoparticle or polymeric micelle, encapsulating a chemopreventative or chemotherapeutic agent (including, but not limited to, celecoxib, carboplatin, paclitaxel, cisplatin, 5-fluorouracil (5-FU), oxaliplatin, capecitabine, chlorambucil, sorabenib and irinotecan).

In some embodiments, the regent comprises at least one detectable label attached to the peptide or multimer form of the peptide and at least one therapeutic moiety attached to the peptide or multimer form of the peptide.

In another aspect, the disclosure provides a composition comprising a reagent of the invention and a pharmaceutically acceptable excipient.

In yet another aspect, the disclosure provides methods for detecting epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) in a patient comprising the steps of administering a reagent of the invention to the patient and detecting binding of the reagent to cancerous cells.

In another aspect, the disclosure provides a method of determining the effectiveness of a treatment for cancer and/or cancer metastasis, or recurrence of cancer in a patient comprising the step of administering a reagent of the invention to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, the methods further comprise obtaining a biopsy of the cells labeled by the reagent.

In yet another aspect, the disclosure provides a method for delivering a therapeutic moiety to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) in a patient comprising the step of administering a reagent of the invention to the patient.

In a further aspect, the disclosure provides a kit for administering a composition of the invention to a patient in need thereof, comprising the composition, instructions for use of the composition and a device for administering the composition to the patient.

In another aspect, the disclosure provides a peptide consisting of the amino acid sequence SRRPASFRTARE (SEQ ID NO: 1).

BRIEF DESCRIPTION OF THE DRAWINGS

FIG. 3M) Fluorescence intensities were fit to an ANOVA model with terms for 12 means. Signal was quantified from an average of 3 cells chosen randomly from 3 slides for each condition. P-values are shown above data, and compare differences in intensity with addition of unlabeled SRR* and SPS* at each concentration with the same difference with no unlabeled peptide. FIG. 3N) Using flow cytometry, we measured an apparent dissociation constant of $k_d=68$ nM, $R^2=0.96$, and FIG. 3O) an apparent association time constant of $k=0.16$ min$^{-1}$ (6.2 min) for binding of SRR*-Cy5.5 to QhTERT cells that express FGFR2c. These results are representative of 3 independent experiments.

(p-FGFR), downstream AKT (p-AKT) and ERK (p-ERK), especially in QhTERT cells expressing FGFR2c.

Figure 6:
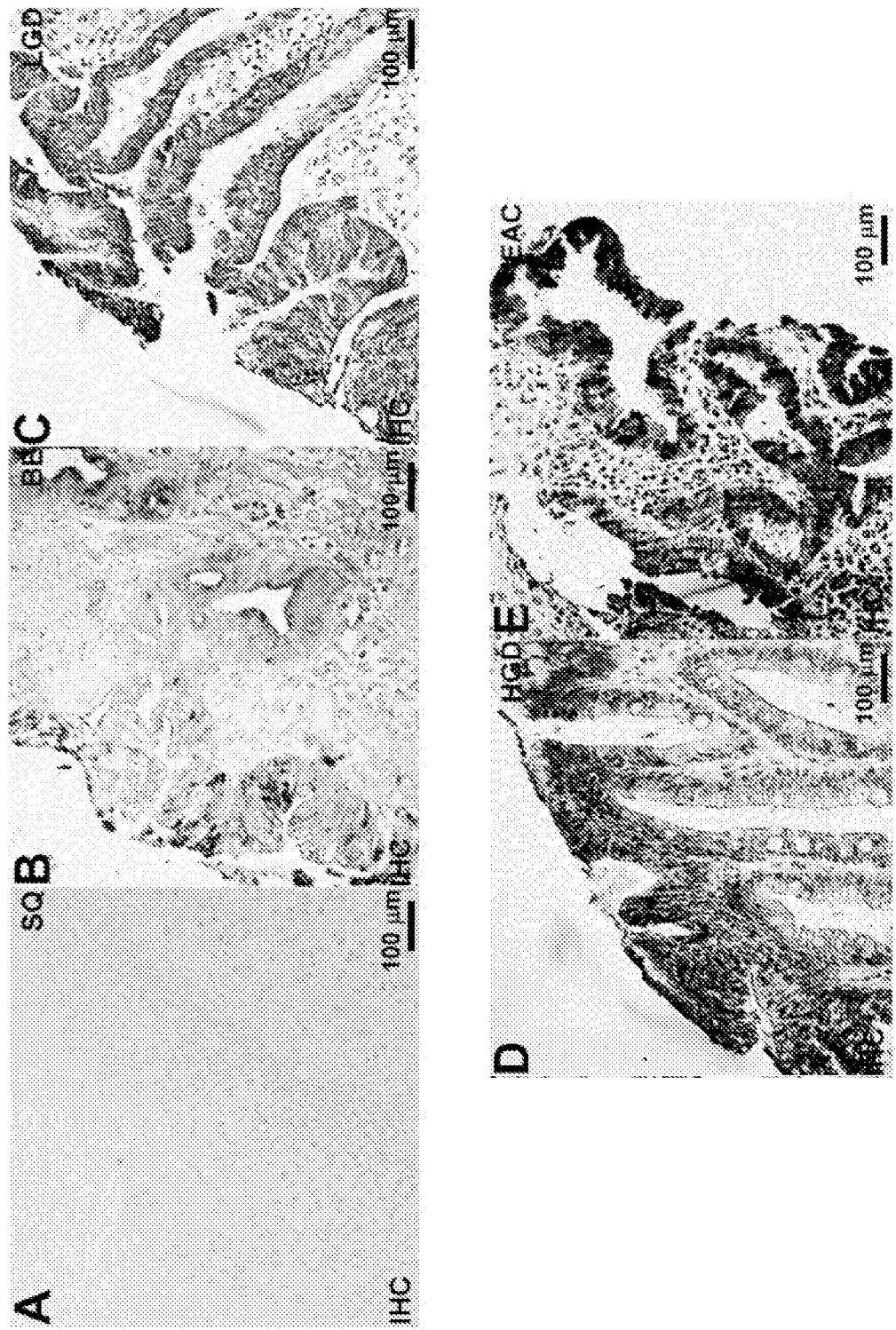

FIG. 6 shows representative IHC from sections of human esophagus ex vivo shows increasing expression of FGFR2 with histological progression from A) squamous (SQ), B) Barrett's esophagus (BE), C) low-grade dysplasia (LGD), D) high-grade dysplasia (HGD), and E) esophageal adenocarcinoma (EAC).

Figure 7:
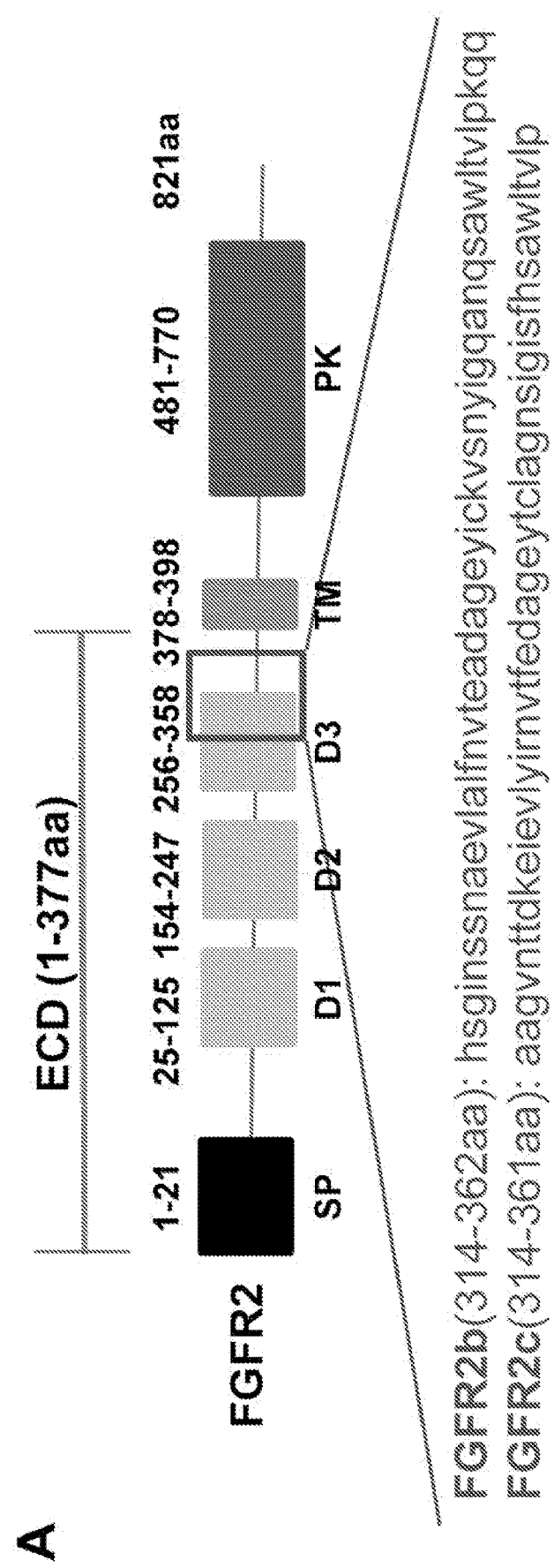
Figure 7:
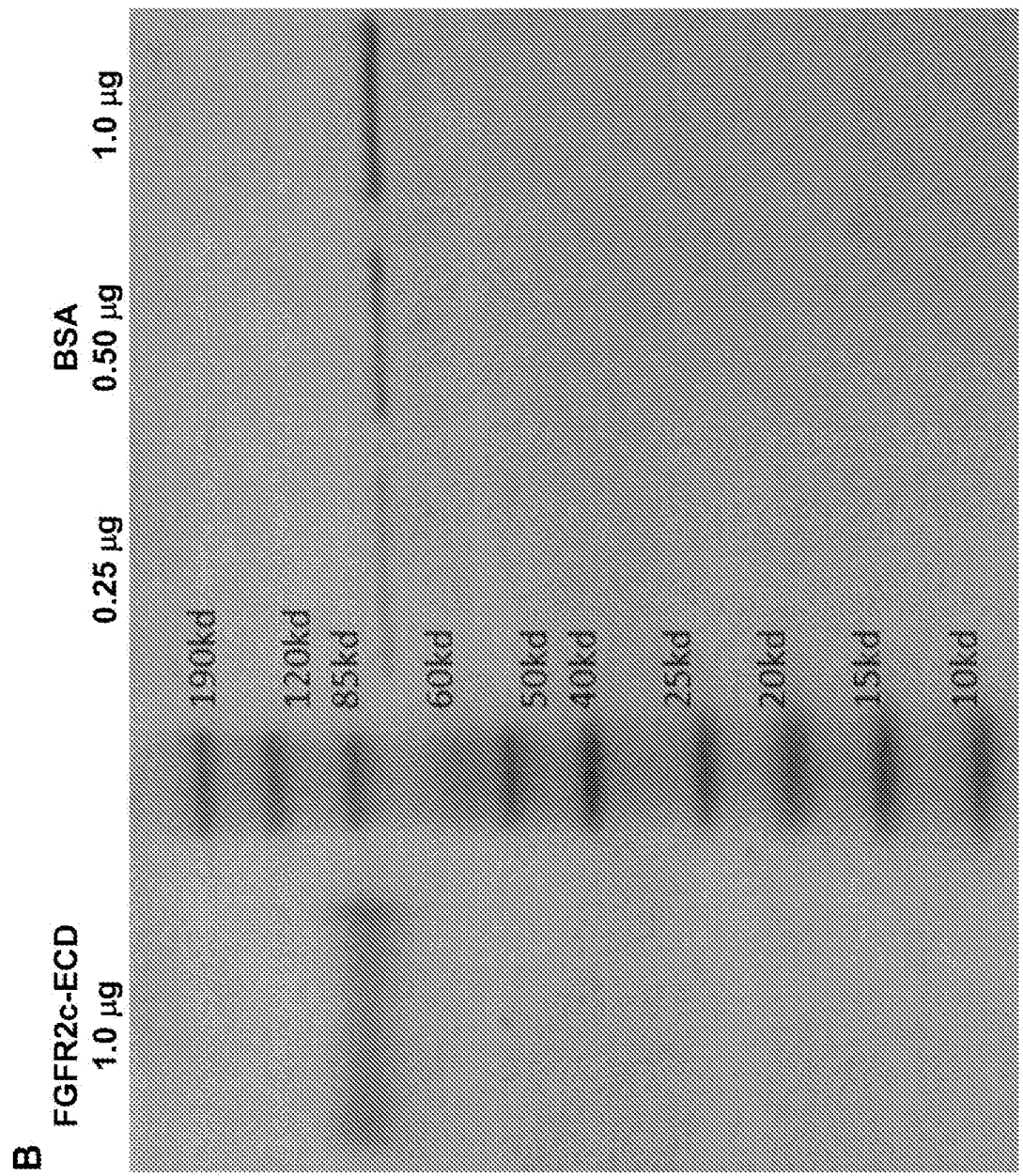

FIG. 7 shows the characterization of FGFR2 extracellular domain (ECD). A) Schematic diagram shows that FGFR2-ECD contains a signal peptide (SP) and 3 extracellular immunoglobulin-like domains (D1-D3). FGFR2-ECD is anchored by a hydrophobic transmembrane region (TM) to the cytoplasmic domain that contains a tyrosine kinase catalytic domain (PK). Alternative splicing of FGFR2 in either exon 8 or 9 results in expression of either FGFR2b or FGFR2c, respectively, in the C-terminus of D3. The differences in amino acids 314-362 is shown (red). B) For recombinant FGFR2-ECD, we achieved a purity >97% by HPLC. Using SDS-PAGE, we observed an apparent molecular mass of ~65-75 kDa that depends on glycosylation. Standard BSA is shown for comparison.

Figure 8:

FIG. 8 shows an experimental mass-to-charge (m/z) ratio of 2385.31 for both SRR*-Cy5.5 and SPS*-Cy5.5. These results agree with expected values.

Figure 9:
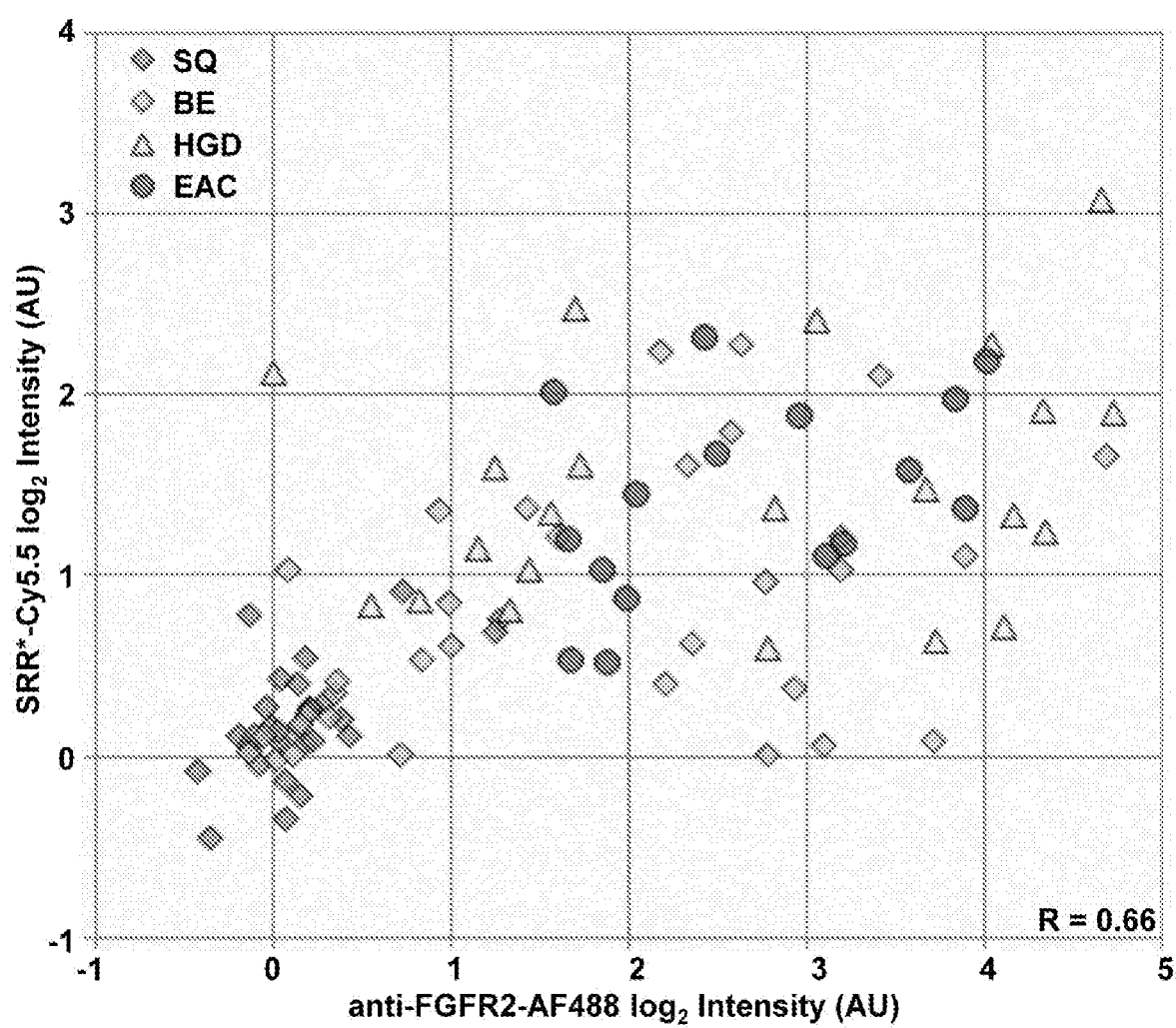

FIG. 9 shows using immunofluorescence a good correlation between SRR*-Cy5.5 peptide and AF488-labeled anti-FGFR2 antibody. We measured an overall Pearson's coefficient of p=0.66, $P=1.4 \times 10^{-13}$ for staining of n=28, 33, 22, and 17 human esophageal specimens of SQ, BE, HGD, and EAC, respectively.

Figure 10:
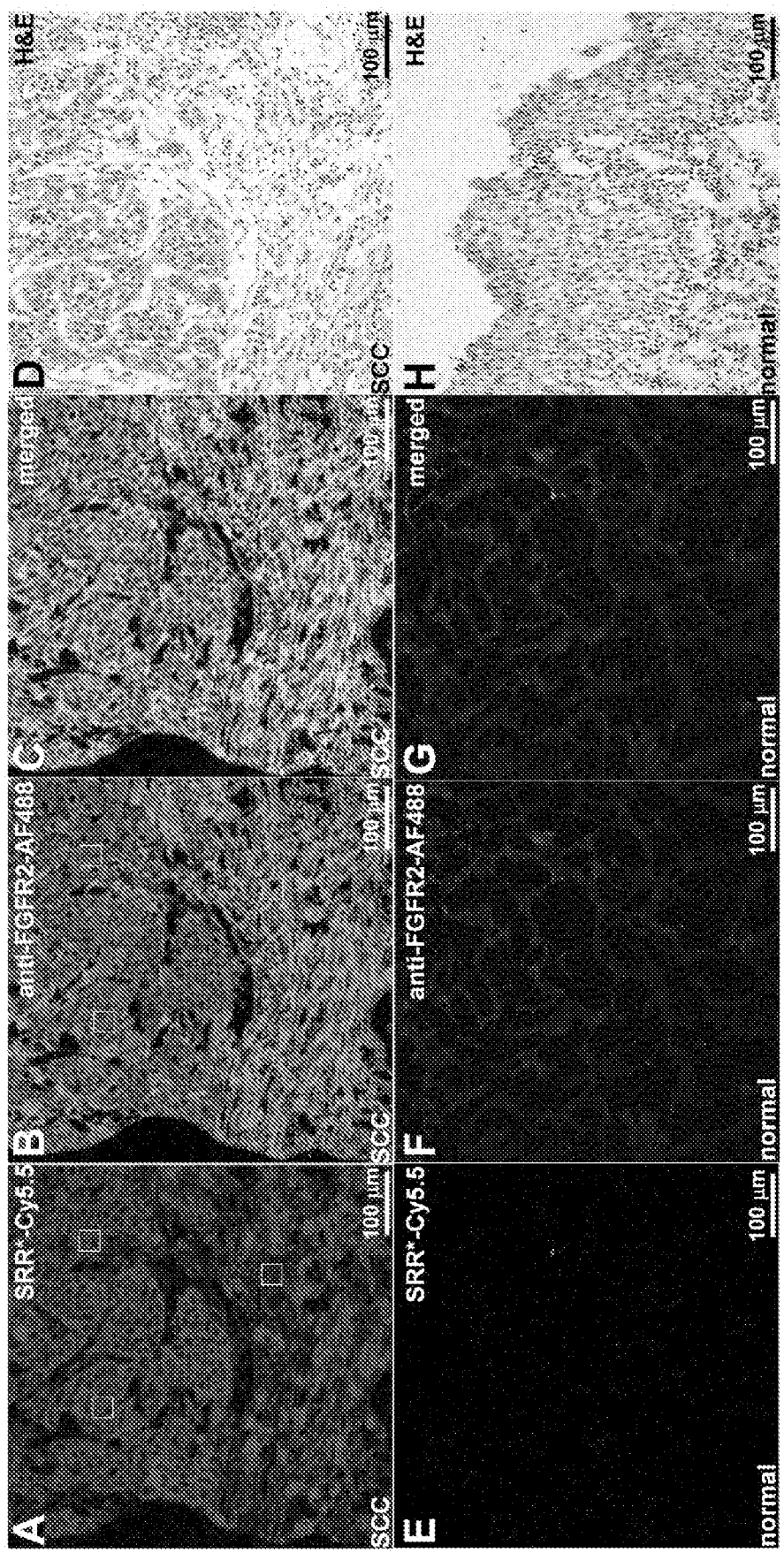
Figure 10:
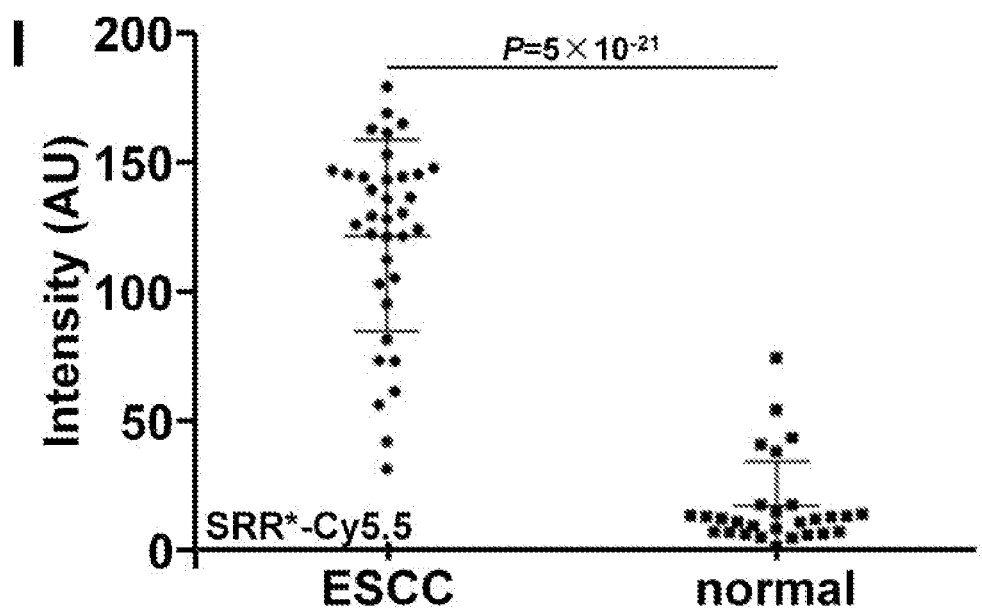
Figure 10:
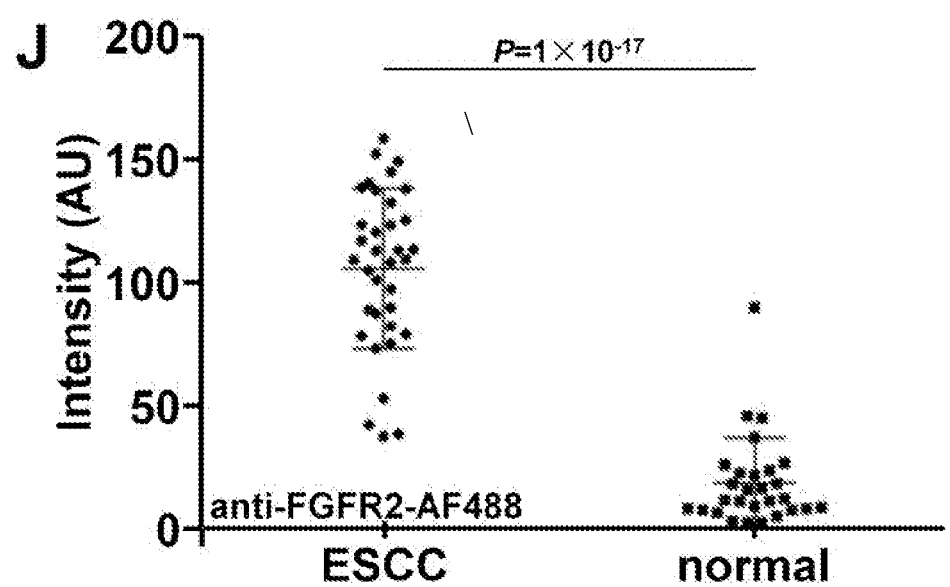

FIG. 10 shows binding of FGFR2 peptide reagent to human esophageal squamous cell carcinoma (SCC). On representative images collected with confocal microscopy, A) SRR*-Cy5.5 (red) and B) anti-FGFR2 antibody labeled with AF488 (green) shows strong binding to sections of human esophageal SCC. C) Pearson's correlation coefficient of p=0.84 was found on merged image. D) Corresponding histology (H&E) for SCC. By comparison, we found minimal staining with E) SRR*-Cy5.5 and F) AF488-labeled anti-FGFR2 antibody to sections of normal human esophagus. G) Merged image. H) Corresponding histology (H&E) of normal esophagus. We quantified the fluorescence intensities from the mean of a set of 3 boxes with dimensions of 30×30 µm² placed randomly, shown in panels A) and B). We found significantly greater mean fluorescence intensity from SCC versus normal for I) SRR*-Cy5.5, $P=5 \times 10^{-21}$ and J) AF488-labeled anti-FGFR2 antibody, $P=1 \times 10^{-17}$, by paired, two-sided t-test.

Figure 11:
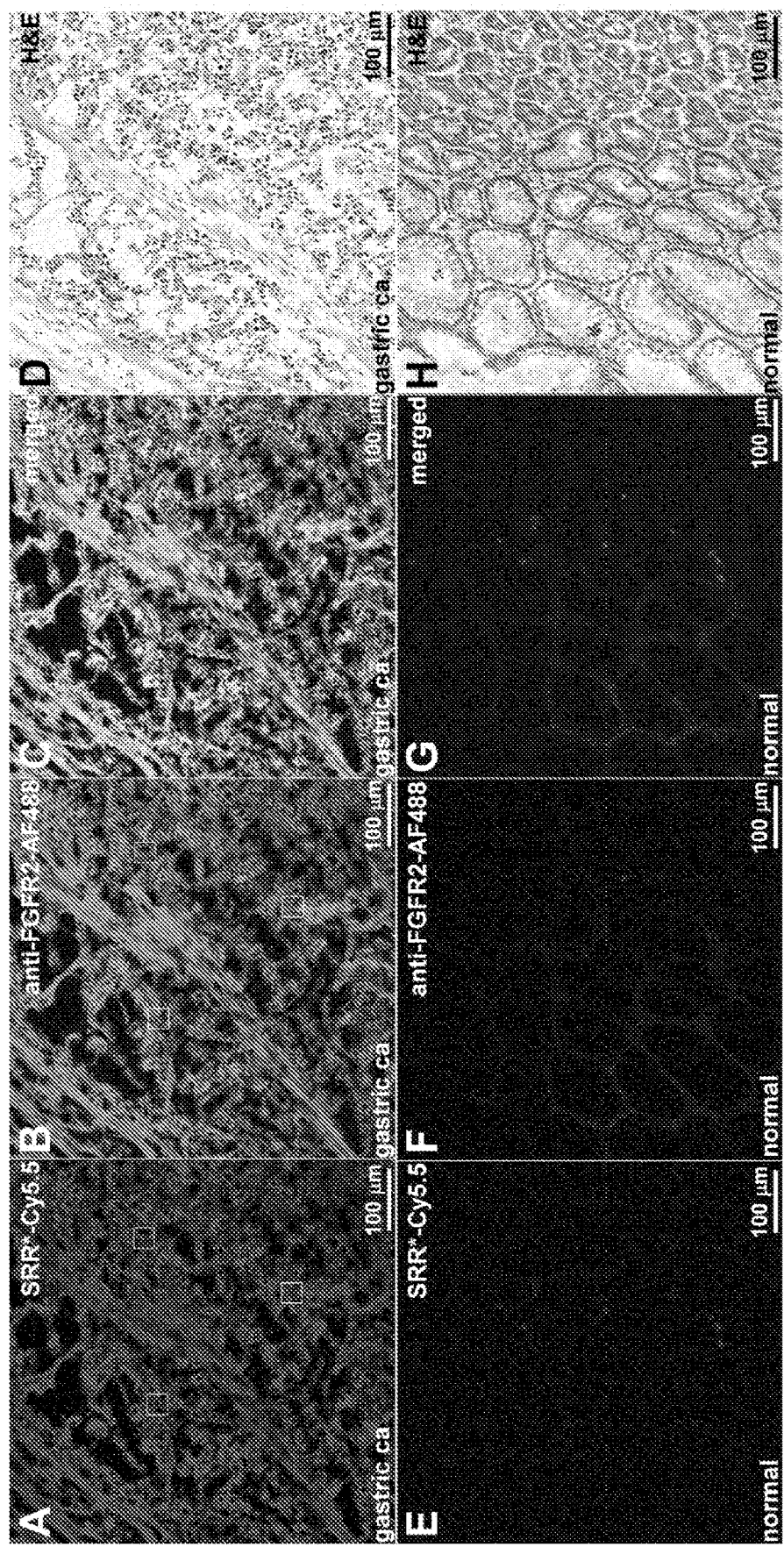
Figure 11:
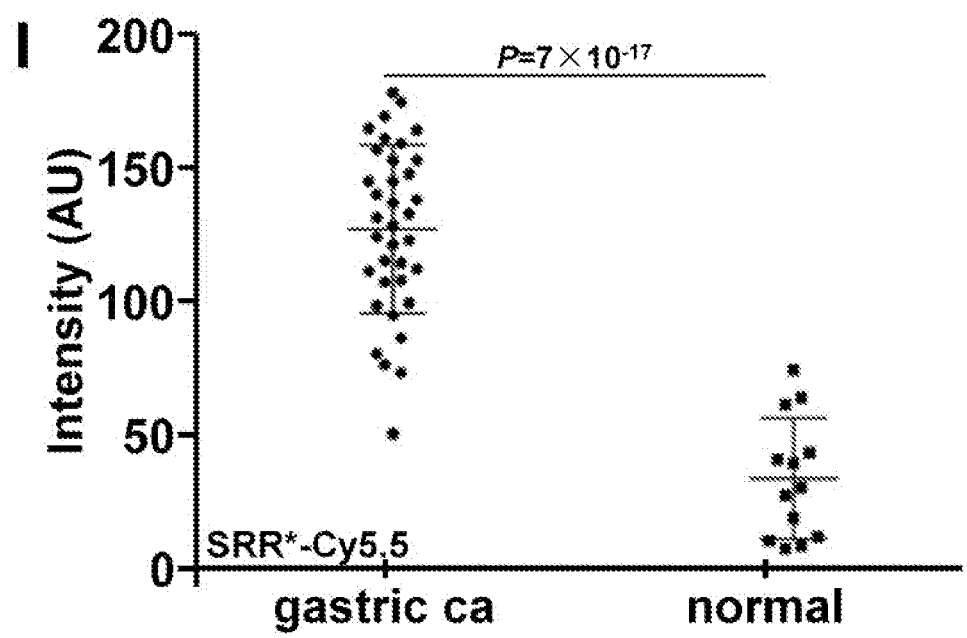
Figure 11:
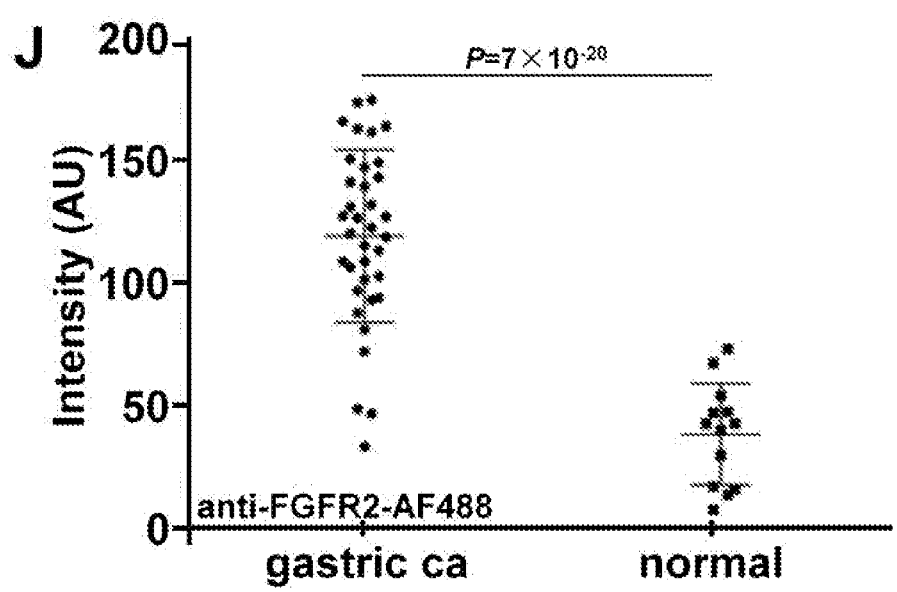

FIG. 11 shows binding of FGFR2 peptide reagent to human gastric cancer. On representative images collected with confocal microscopy, A) SRR*-Cy5.5 (red) and B) anti-FGFR2 antibody labeled with AF488 (green) shows strong binding to sections of human gastric cancer. C) Pearson's correlation coefficient of p=0.93 was found on merged image. D) Corresponding histology (H&E) for gastric cancer. By comparison, we found minimal staining with E) SRR*-Cy5.5 and F) AF488-labeled anti-FGFR2 antibody to sections of normal human stomach. G) Merged image. H) Corresponding histology (H&E) of normal stomach. We quantified the fluorescence intensities from the mean of a set of 3 boxes with dimensions of 30×30 µm² placed randomly, shown in panels A) and B). We found significantly greater mean fluorescence intensity from gastric cancer versus normal for I) SRR*-Cy5.5, $P=7 \times 10^{-17}$ and J) AF488-labeled anti-FGFR2 antibody, $P=7 \times 10^{-20}$, by paired, two-sided t-test.

DESCRIPTION

Image-guided surgery that targets overexpression of molecules that are specific for epithelial-derived cancers can help achieve a balance between complete tumor resection and maintenance of tissue function. Targeted imaging can also help maximize the remaining volume of "normal" tissue to optimize post-operative function. In addition, imaging targets specific for epithelial-derived cancers can serve as important biomarkers for evaluating patient prognosis. Imaging reagents can provide a biological basis for disease detection, prognosis, guide therapy, and monitor treatment response. Antibodies have been most commonly used, however they are large in size, high in molecular weight, and have long plasma half-lives, all leading to increased background on imaging. Peptides are attractive imaging tools, with a small size and low molecular weight that result in improved properties for deep tissue imaging inaccessible to antibodies. Peptides are less immunogenic, clear from non-target tissues to reduce background, and can be synthesized for improved binding affinity. All of this promotes deep tissue penetration and effective targeting.

In one aspect, the disclosure provides peptides that bind to FGFR2 expressed on dysplastic cells and/or cancerous cells. The peptides include, but are not limited to, the peptide SRRPASFRTARE (SEQ ID NO: 1).

In a further aspect, the disclosure provides reagents comprising a peptide of the invention. A "peptide reagent" of the invention comprises at least two components, a peptide of the invention and another moiety attached to the peptide. The only component of the reagent that contributes to binding of FGFR2 is the peptide of the invention. In other words, the reagent "consists essentially of" a peptide of the invention. In some embodiments, the other moiety comprises amino acids but the peptide of the invention is not linked to those amino acids in nature and the other amino acids do not affect binding of the peptide to FGFR2. Moreover, the other moiety in a reagent contemplated herein is not a phage in a phage display library or a component of any other type of peptide display library.

In some embodiments, the reagents comprise at least one detectable label as a moiety attached to a peptide of the invention. The detectable label may be detectable, for example, by optical, ultrasound, PET, SPECT, or magnetic resonance imaging. In some embodiments the label detectable by optical imaging is fluorescein isothiocyanate (FITC), Cy5, Cy5.5 or IRdye800 (also known as IR800CW).

In some embodiments, the detectable label is attached to a peptide of the invention by a peptide linker. The terminal amino acid of the linker can be a lysine such as in the exemplary linker GGGSK (SEQ ID NO: 2).

In some embodiments, the reagents comprise at least one therapeutic moiety attached to a peptide of the invention. The therapeutic moiety may be a chemopreventative or chemotherapeutic agent. In certain embodiments, the chemopreventative agent is celecoxib. In certain embodiments, the chemotherapeutic agent is carboplatin, paclitaxel, cisplatin, 5-fluorouracil (5-FU), oxaliplatin, capecitabine, chlorambucil, sorafenib or irinotecan. In some embodiments, the therapeutic moiety is a nanoparticle or micelle encapsulating another therapeutic moiety. In certain embodiments, carboplatin, paclitaxel, cisplatin, 5-fluorouracil (5-FU), oxaliplatin, capecitabine, chlorambucil, sorafenib or irinotecan are encapsulated.

In some embodiments, the regent comprises at least one detectable label attached to the peptide or multimer form of the peptide, and at least one therapeutic moiety attached to the peptide or multimer form of the peptide.

In yet a further aspect, the disclosure provides a composition comprising a reagent of the invention and a pharmaceutically acceptable excipient.

In still a further aspect, the disclosure provides a method for specifically detecting epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) in a patient comprising the steps of administering a reagent of the invention attached to a detectable label to the patient and detecting binding of the reagent to the cells. In some embodiments, the detectable binding takes place in vivo. In others, the detectable binding takes places in vitro. In still others, the detectable binding takes place in situ.

The phrase "specifically detects" means that the reagent binds to and is detected in association with a type of cell, and the reagent does not bind to and is not detected in association with another type of cell at the level of sensitivity at which the method is carried out.

In an additional aspect, the disclosure provides a method of determining the effectiveness of a treatment for epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) and/or cancer metastasis, or recurrence of cancer in a patient comprising the step of administering a reagent of the invention attached to a detectable label to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, 0%, a 70%, about 75%, about 80%, about 85%, about 90%, about 95% or more is indicative of effective treatment. In some embodiments, the method further comprises obtaining a biopsy of the cells labeled by the reagent.

In another aspect, the disclosure provides a method for delivering a therapeutic moiety to a patient comprising the step of administering a reagent of the invention attached to a therapeutic moiety to the patient.

In yet another aspect, the disclosure provides a method for delivering a therapeutic moiety to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) of a patient comprising the step of administering a reagent of the invention attached to a therapeutic moiety to the patient.

In still another aspect, the disclosure provides a kit for administering a composition of the invention to a patient in need thereof, where the kit comprises a composition of invention, instructions for use of the composition and a device for administering the composition to the patient.

Linkers, Peptides and Peptide Analogs

As used herein, a "linker" is a sequence of amino acids located at the C-terminus of a peptide of the disclosure. In some embodiments, the linker sequence terminates with a lysine residue.

In some embodiments, the presence of a linker results in at least a 1% increase in detectable binding of a reagent of the invention to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science,* 249:386-390 (1990)]. The protein coat of bacteriophage, such as the filamentous M13 or icosahedral T7, is genetically engineered to express a very large number ($>10^9$) of different polypeptides with unique sequences to achieve affinity binding [Cwirla et al., *Proc. Natl. Acad. Sci. USA,* 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature,* 380:364-366 (1996)]. The polypeptides that preferentially bind to FGFR2 are optionally labeled with fluorescence dyes, including but not limited to, FITC, Cy 5.5, Cy 7, and Li-Cor.

Peptides include D and L forms, either purified or in a mixture of the two forms. Also contemplated by the present disclosure are peptides that compete with peptides of the invention for binding to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach).

In some embodiments, a peptide of a reagent of the invention is presented in multimer form. Various scaffolds are known in the art upon which multiple peptides can be presented. In some embodiments, a peptide is presented in multimer form on a trilysine dendritic wedge. In some embodiments, a peptide is presented in dimer form using an aminohexanoic acid linker. Other scaffolds known in the art include, but are not limited to, other dendrimers and polymeric (e.g., PEG) scaffolds.

It will be understood that peptides and linkers of the invention optionally incorporate modifications known in the art and that the location and number of such modifications are varied to achieve an optimal effect in the peptide and/or linker analog.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable to the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative ammo acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) in comparison to the parent peptide.

Detectable Markers

As used herein, a "detectable marker" is any label that can be used to identify the binding of a composition of the disclosure to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach). Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the invention include, but are not limited to, FITC, Cy5, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, C5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1, Ca saturated, IDRdye800 (IR800CW), JC-1, JC-1 pH 8.2, Lissamine rhodamine, *Lucifer* Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}C$, $^{13}N$, $^{15}O$, $^{18}F$, $^{32}P$, $^{52}Fe$, $^{62}Cu$, $^{64}Cu$, $^{67}Cu$, $^{67}Ga$, $^{68}Ga$, $^{86}Y$, $^{89}Zr$, $^{90}Y$, $^{94}mTc$, $^{94}Tc$, $^{95}Tc$, $^{99}mTc$, $^{103}Pd$, $^{105}Rh$, $^{109}Pd$, $^{111}Ag$, $^{111}In$, $^{123}I$, $^{124}I$, $^{125}I$, $^{131}I$, $^{140}La$, $^{149}Pm$, $^{153}Sm$, $^{154-159}Gd$, $^{165}Dy$, $^{166}Dy$, $^{166}Ho$, $^{169}Yb$, $^{175}Yb$, $^{175}Lu$, $^{177}Lu$, $^{186}Re$, $^{188}Re$, $^{192}Ir$, $^{198}Au$, $^{199}Au$, and $^{212}Bi$.

For positron emission tomography (PET) tracers including, but not limited to, carbon-11, nitrogen-13, oxygen-15 and fluorine-18 are used.

A worker of ordinary skill in the art will appreciate that there are many such detectable markers that can be used to visualize a cell, in vitro, in vivo or ex vivo.

Therapeutic Moieties

Therapeutic moieties contemplated by the invention include, but are not limited to polypeptides (including protein therapeutics) or peptides, small molecules, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some embodiments, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In some embodiments, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in some embodiments, chemotherapeutic agents. A chemotherapeutic agent contemplated for use in a reagent of the invention includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, capecitabine, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophyllotoxins such as etoposide and teniposide; antibiotics such as actinomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; topoisomerase inhibitors such as irinotecan; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Chemotherapeutic agents such as gefitinib, sorafenib and erlotinib are also specifically contemplated.

Therapeutic moieties to be attached to a peptide described herein also include nanoparticles or micelles that, in turn, encapsulate another therapeutic moiety. In some embodiments, the nanoparticles are polymeric nanoparticles such as described in Zhang et al., *ACS NANO*, 2(8): 1696-1709 (2008) or Zhong et al., *Biomacromolecules*, 15: 1955-1969 (2014). In some embodiments, the micelles are polymeric micelles such as octadecyl lithocholate micelles described in Khondee et al., *J. Controlled Release*, 199: 114-121 (2015) and U.S. Provisional Patent Application No. 62/262,195. In some embodiments, the peptide reagents comprising nanoparticles or micelles encapsulate carboplatin, paclitaxel, cisplatin, 5-fluorouracil (5-FU), oxaliplatin, capecitabine or irinotecan.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to epithelial-derived cancer cells (including, but not limited to, breast, colorectal, esophagus adenocarcinoma, esophagus squamous cell carcinoma, gastroesophageal junction adenocarcinoma (GEJAC), pancreas, prostate, thyroid and stomach) is by any means known to those of ordinary skill in the art. As discussed herein, visualization is, for example and without limitation, in vivo, in vitro, or in situ visualization.

In some embodiments where the detectable label is a radiolabel, the radiolabel is detected by nuclear imaging.

In some embodiments where the detectable label is a fluorophore, the fluorophore is detected by near infrared (NIR) fluorescence imaging.

Some embodiments of methods of the invention involve the acquisition of a tissue sample from a patient. The tissue sample is selected from the group consisting of a tissue or organ of said patient.

Formulations

Compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one reagent as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

The invention will be more fully understood by reference to the following examples which detail exemplary embodiments of the invention.

The incidence of esophageal adenocarcinoma (EAC) is rising rapidly, and early detection in the precursor state of Barrett's esophagus (BE) is challenged by pre-malignant lesions that are difficult detect with conventional endoscopic surveillance. Expression of fibroblast growth factor receptor 2 (FGFR2) is an early event in progression of BE to EAC, and is a promising imaging target. As described in the examples below, we used phage display to identify the peptide SRRPASFRTARE that binds specifically to the extracellular domain of FGFR2. We labeled this peptide with a near-infrared fluorophore Cy5.5, and validated the specific binding to FGFR2 overexpressed in cells in vitro. We found high affinity $k_d$=67.94 nM and rapid binding k=0.16 min$^{-1}$ (6.2 min). In specimens of human esophagus, we found significantly greater peptide reagent binding to high-grade dysplasia (HGD) versus either BE or normal squamous epithelium, and good correlation with anti-FGFR2 antibody. We also observed significantly greater peptide reagent binding to excised specimens of esophageal squamous cell carcinoma and gastric cancer compared to normal mucosa. These results support the use of this FGFR2 peptide reagent as a clinical imaging agent to guide tissue biopsy and improve methods for early detection of EAC and other epithelial-derived cancers.

Tissues, Cells, and Chemicals

All human esophagus specimens were obtained with written, informed patient consent per approval and guidelines of the University of Michigan Institutional Review Board (IRB). Human non-dysplastic Barrett's esophagus (BE) cells immortalized with hTert (QhTERT) were obtained from the American Type Culture Collection (ATCC) and cultured in keratinocyte-serum free medium containing bovine pituitary extract and human recombinant EGF (ThermoFisher #17005042). QhTERT cells with stable expression of FGFR2b or FGFR2c were provided by DGB. We cultured these cells with keratinocyte-serum free medium containing bovine pituitary extract and human recombinant EGF (ThermoFisher #17005042) and added 1 μg/mL of puromycin-dihydrochloride (Invitrogen #A11138-03). All cells were cultured at 37° C. in 5% $CO_2$, and were passaged using 0.25% EDTA containing trypsin (Mediatech Inc). A hemocytometer was used to count the cell number. Peptide synthesis reagents were obtained from either Anaspec or AAPPTEC with the highest grade available (>99% purity) and used without further purification. Solvents and other chemical reagents were obtained from Sigma-Aldrich, unless otherwise stated.

Example 1

Expression of FGFR2

We performed immunohistochemistry (IHC) on specimens of human esophagus, including squamous (SQ), Barrett's esophagus (BE), low-grade dysplasia (LGD), high-grade dysplasia (HGD), and esophageal adenocarcinoma (EAC), that were classified by an expert gastrointestinal pathologist (HDA) to demonstrate representative levels of FGFR2 expression, FIG. 6.

Example 2

Peptides Specific for FGFR2

A peptide specific for FGFR2 was identified using phage display technology.

The extra-cellular domain (ECD) of FGFR2 consists of a signal peptide (SP) and 3 extracellular immunoglobulin-like domains (D1-D3), FIG. 7A. We performed peptide selection using the extracellular domain (ECD) of FGFR2c. This region of the target is accessible to imaging. We obtained recombinant FGFR2-ECD (Met1-Glu377) consisting of 367 amino acids after removal of the signal peptide (#10824-H08H-50, Sino Biological). We performed SDS-PAGE with 1 μg of FGFR2-ECD to evaluate the quality and quantity using 0.25, 0.5, and 1 μg of BSA as control. We used FGFR2-ECD with purity >97% by HPLC. SDS-PAGE shows apparent molecular mass of ~65-75 kDa, FIG. 7B. This result is slightly higher than the expected value of 41 kDa as a result of glycosylation.

Peptide selection was performed using a phage display library (New England Biolabs, Ph.D.-12) per manufacturer instructions. This library consists of M13 bacteriophage that expresses ~$10^9$ unique 12-amino acid sequences. $2\times10^{11}$ pfu consisting of $2\times10^9$ unique clones with ~100 copies each were biopanned against FGFR2-ECD immobilized in a 6-well plate at 4° C. Four rounds of biopanning were performed using a decreasing quantity (100, 80, 60, and 40 μg) of FGFR2-ECD in successive rounds to increase binding specificity. After the 4th round, 50 plaques were randomly selected for DNA preparation and sequence analysis. We used an ABI Automatic DNA Analyzer (Applied Biosystems) with primer 5'-CCCTCATAG TTA GCG TAA CG-3'

(-96 gIII sequencing primer, New England Biolabs) that corresponds to the pIII gene sequence of the M13 phage.

After the four rounds of biopanning with phage display, we found two sequences that showed enrichment. In 50 clones, SRRPASFRTARE (SEQ ID NO: 1) appeared fifteen times and GLHTSATNLYLH (SEQ ID NO: 3) appeared four times. GLHTSATNLYLH (SEQ ID NO: 3) was found previously when we biopanned against other protein targets, and is likely an unrelated sequence.

A structural model was used to optimize the sequence of the SSR peptide for maximum binding affinity to FGFR2. See, Macindoe et al., Nucleic Acids Research, 38(S2): W445-W449 (2010). Peptide alignment to the target was evaluated by rotating the receptor and ligand about their centers of mass over a full range of intermolecular distances and rotational angles [Svensson et al., J Biol Chem, 287: 14040-14051 (2012)]. Several mutations of the lead peptide sequence were compared to achieve the lowest docking energy, aiming to achieve a value of $E_t<-600$. Scrambled peptides were also developed using the structural model for use as controls.

We synthesized the 12 amino acid sequence SRRPASFR-TARE (SEQ ID NO: 1) (black) and attached the fluorophore Cy5.5 (red) via a GGGSK linker (SEQ ID NO: 2) (blue) on the C-terminus to generate the reagent referred to hereinafter as SRR*-Cy5.5, FIG. 1A. Cy5.5 was chosen for photostability and high quantum yield in the near-infrared (NIR) spectrum.[23] We used a linker to prevent steric hindrance of the peptide by the dye.

Standard Fmoc-mediated solid-phase synthesis was used to produce the Cy5.5-labeled peptide reagent.[44] We assembled Fmoc and Boc protected L-amino acids on rink amide MBHA resin. The peptides were synthesized using a PS3 automatic synthesizer (Protein Technologies Inc). The C-terminal lysine was incorporated as Fmoc-Lys (ivDde)-OH, and the N-terminal amino acid was incorporated with Boc protection to avoid unwanted Fmoc removal during deprotection of the ivDde moiety prior to fluorophore labeling. Upon complete assembly of the peptide, the resin was transferred to a reaction vessel for manual labeling with dye. The ivDde side chain protecting group was removed with 5% hydrazine in DMF (3×10 min) with continuous shaking at room temperature (RT). The resin was washed with dimethylformamide (DMF) and dichloromethane (DCM) 3× each for 1 min. The protected resin-bound peptide was incubated overnight with Cy5.5-NHS ester (Lumiprobe LLC) with DIEA, and the completion of the reaction was monitored by a qualitative Ninhydrin test. Upon completion of labeling, the peptide was cleaved from the resin using TFA:TIS:H2O (95:2.5:2.5 v/v/v; Sigma-Aldrich) for 4 hours with shaking in the dark at RT. After separating the peptide from the resin, the filtrate was evaporated with $N_2$ gas followed by precipitation with chilled diethyl ether and stored overnight at -20° C. The precipitate was centrifuged at 3000 rpm for 5 min and washed with diethyl ether 3× and centrifuged in between each washing step. The crude peptides were dissolved in 1:1 acetonitrile/H2O (v/v) and purified by prep-HPLC with a $C_{18}$ column (Waters Inc) using a water (0.1% TFA)-acetonitrile (0.1% TFA) gradient. The final purity of the peptides was confirmed with an analytical $C_{18}$-column.

Figure 1:
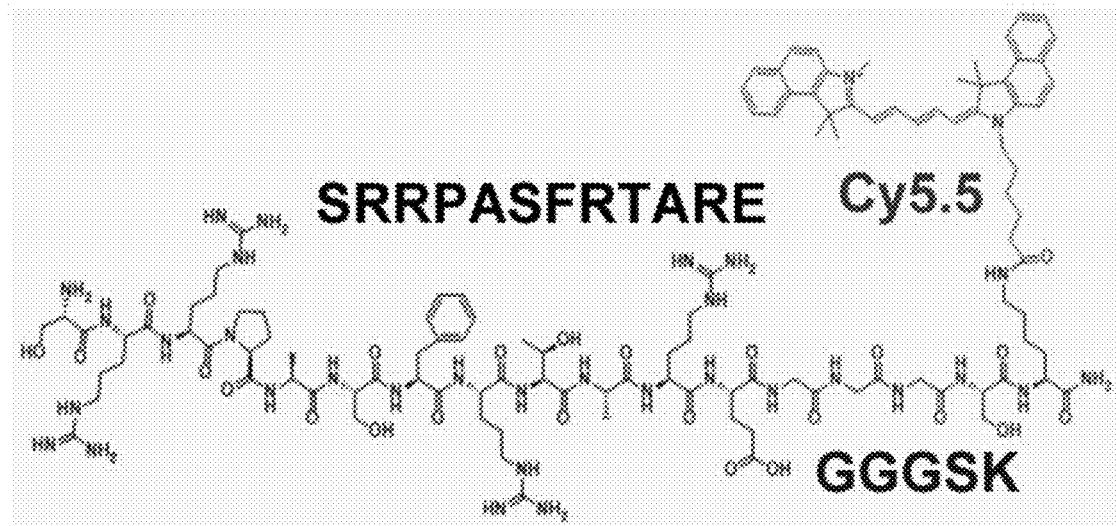
FIG. 1 shows the chemical structure for 12 amino acid (aa) peptide sequence A) SRRPASFRTARE (SRR*) found to be specific for FGFR2, and B) scrambled peptide SPS-RERTFRARA (SPS*) used for control. A Cy5.5 fluorophore (red) is attached via a GGGSK linker (blue) to prevent steric hindrance. C) SRR*-Cy5.5 was found using a structural model (1EV2) to bind to the extracellular domain (ECD) of FGFR2c (147-366 aa) with $E_t=-290.43$ while SPS*-Cy5.5 resulted in $E_t=-277.37$. D) Fluorescence spectra of SRR*-Cy5.5 and SPS*-Cy5.5 at 10 µM concentration in PBS with excitation at $\lambda_{ex}=671$ nm shows peak emission at $\lambda_{em}=710$ nm in the NIR spectrum.
Figure 1:
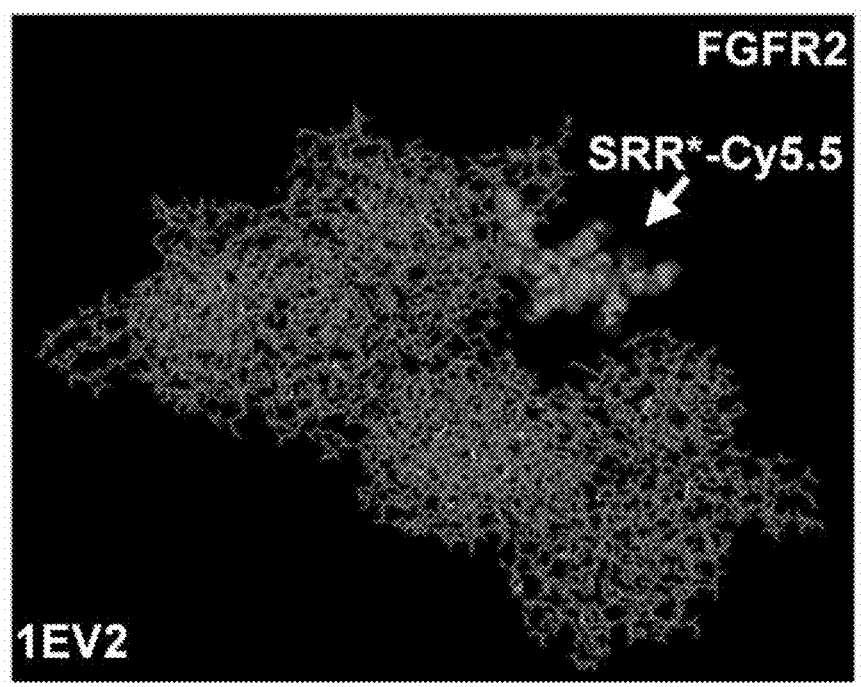
Figure 1:
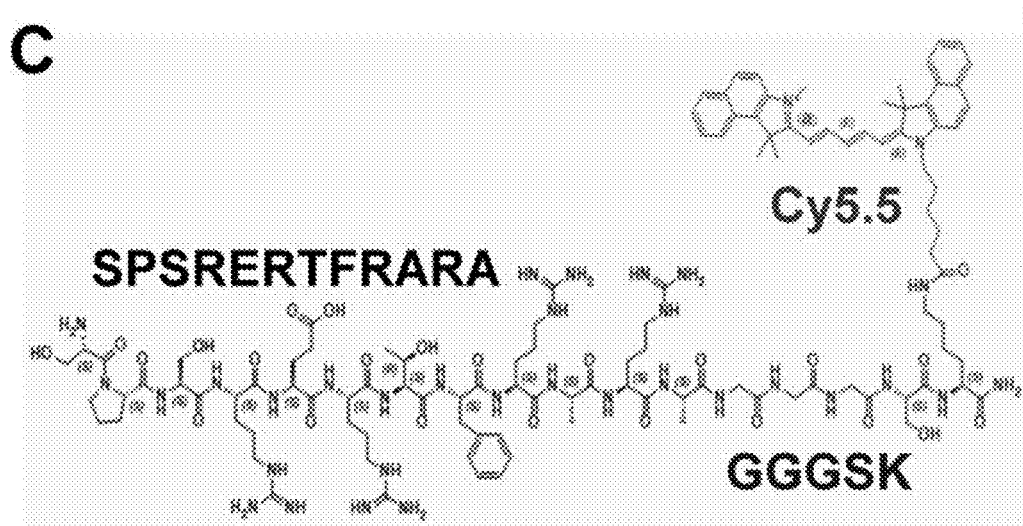
Figure 1:
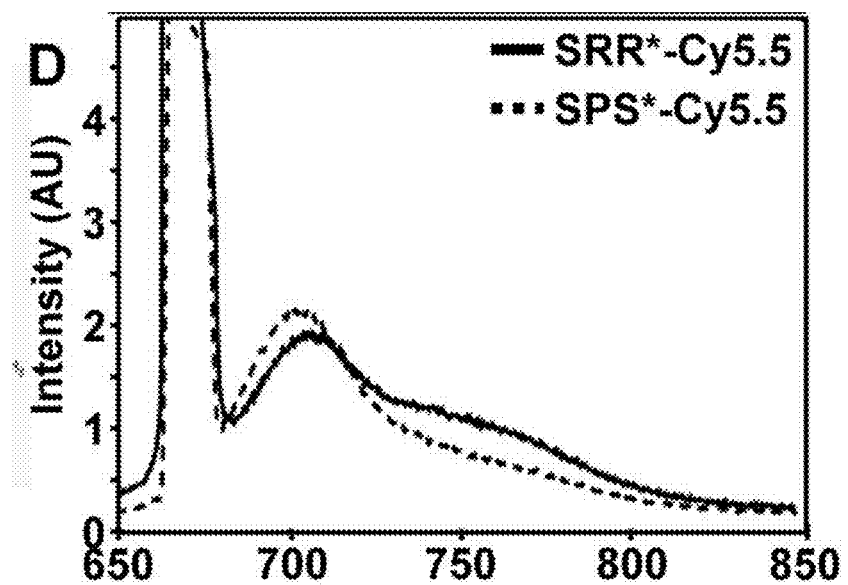

We used a structural model (1EV2),[24] FIG. 1B, and found SRR*-Cy5.5 to bind to domains D2 and D3 of FGFR2-ECD with a total energy $E_t=-290.43$. We also used amino acids 147-366 of this model to develop a scrambled sequence SPSRERTFRARA for control, FIG. 1C. This peptide was also labeled with Cy5.5 via a GGGSK linker, hereafter SPS*-Cy5.5. For SPS*-Cy5.5, we calculated $E_t=-277.37$. The fluorescence spectra of SRR*-Cy5.5 and SPS*-Cy5.5 with $\lambda_{ex}=671$ nm excitation revealed a peak emission at $\lambda_{em}=710$ nm, FIG. 1D. We purified SRR*-Cy5.5 and SRS*-Cy5.5 to >97% on HPLC, and measured an experimental mass-to-charge (m/z) ratio on mass spectrometry of 2385.31 for both peptides that agreed with the expected value, FIG. 8.

Example 3

Confocal Fluorescence Microscopy

Figure 2:
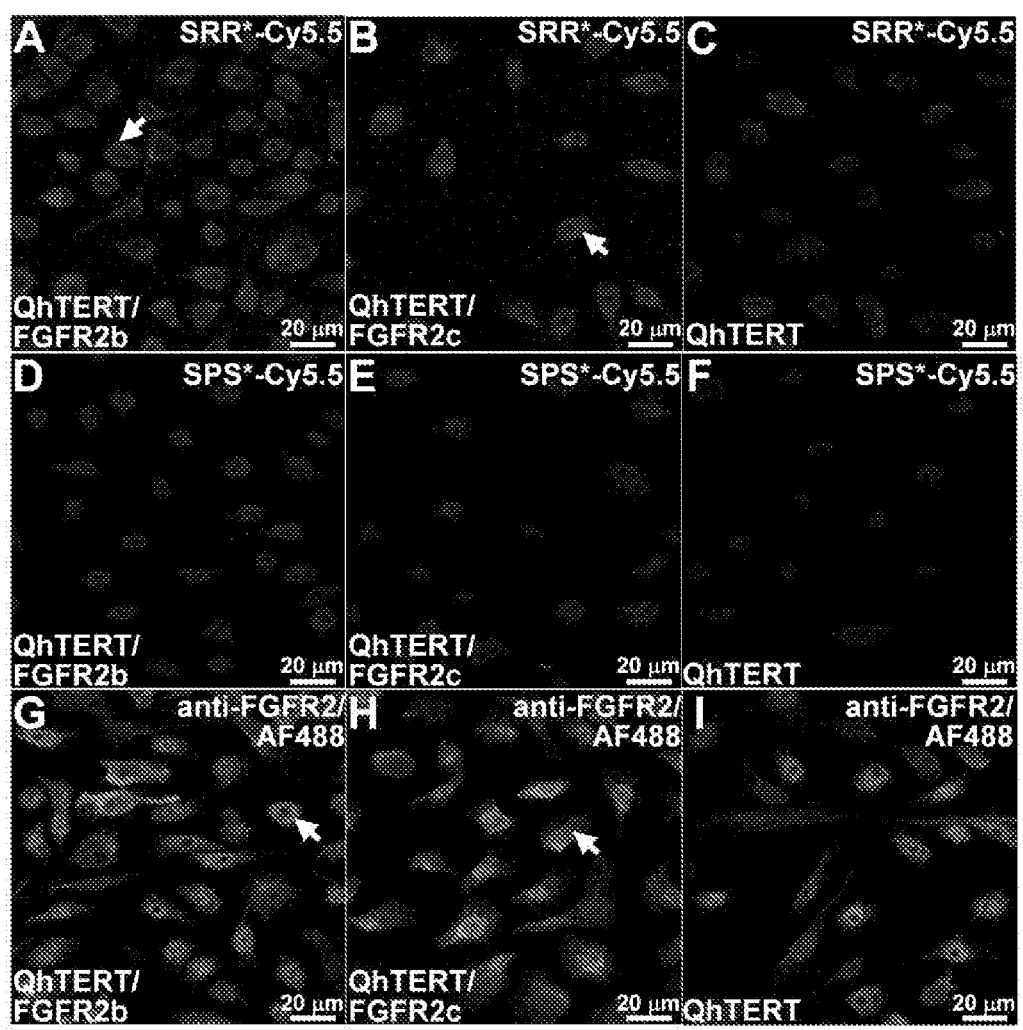
FIG. 2 shows on confocal microscopy strong binding of SRR*-Cy5.5 (red) to surface of QhTERT cells that express A) FGFR2b and B) FGFR2c compared with C) wild type. D-F) Minimal signal is seen with the scrambled peptide SPS*-Cy5.5. G-I) Strong binding is seen with anti-FGFR2 antibody labeled with AF488 (green) used as positive control. All experiments were performed in triplicate. J) Quantified results show significantly higher mean fluorescence intensities for SRR*-Cy5.5 versus SPS*-Cy5.5 (control). We log-transformed and averaged measurements for 3 random cells on each of 3 slides per condition, and fit an ANOVA model with terms for 6 means. K) Western blot shows protein expression level of FGFR2 for each cell.
Figure 2:
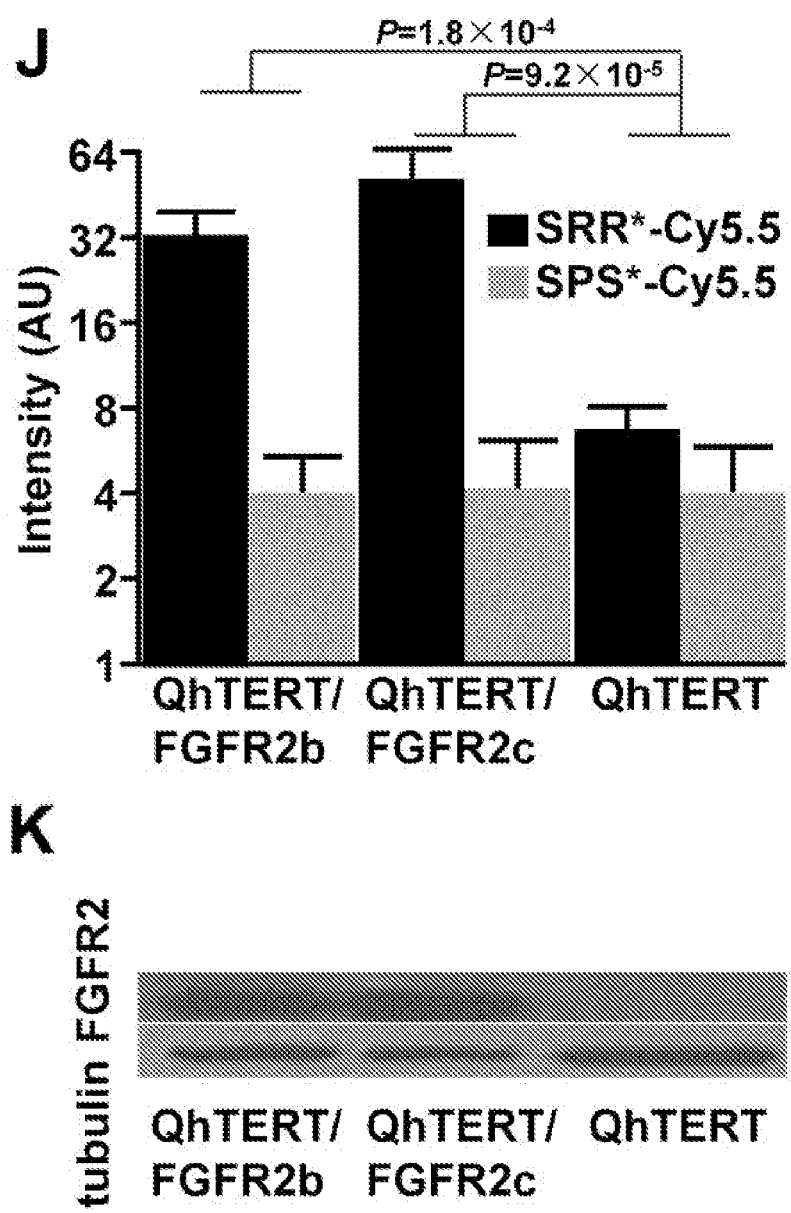

On confocal microscopy, we validated specific peptide reagent binding to human BE cells that express FGFR2. We observed strong signal with SRR*-Cy5.5 on the surface of QhTERT cells that express either FGFR2b or FGFR2c and minimal signal for wild-type, FIG. 2A-C. Minimal binding was observed for the scrambled control peptide SPS*-Cy5.5 with all cells, FIG. 2D-F. We confirmed these findings using anti-FGFR2 antibody labeled with AF488, FIG. 2G-I. We quantified our results, and found a significantly greater mean fluorescence intensity for SRR*-Cy5.5 than for control with QhTERT cells that express either FGFR2b or FGFR2c compared with wild-type, FIG. 2J. Western blot shows of FGFR2 expression level for each cell, FIG. 2K.

Example 4

Competition for Reagent Binding

We administered unlabeled SRR*, and used confocal microscopy to observe competition for binding of SRR*-Cy5.5 to QhTERT cells that express FGFR2c, FIG. 3A-L. Approximately $10^3$ cells were grown to ~70% confluence on cover glass in triplicate. Unlabeled peptides at concentrations of 0, 50, 100, 150, 250, and 500 µM were incubated with the cells for 30 min at 4° C. The cells were washed and incubated with 5 µM of the target peptide for another 30 min at 4° C. The cells were washed and fixed with 4% PFA for 5 min. The cells were washed with PBS and mounted with ProLong Gold reagent containing DAPI (Invitrogen).

Figure 3:
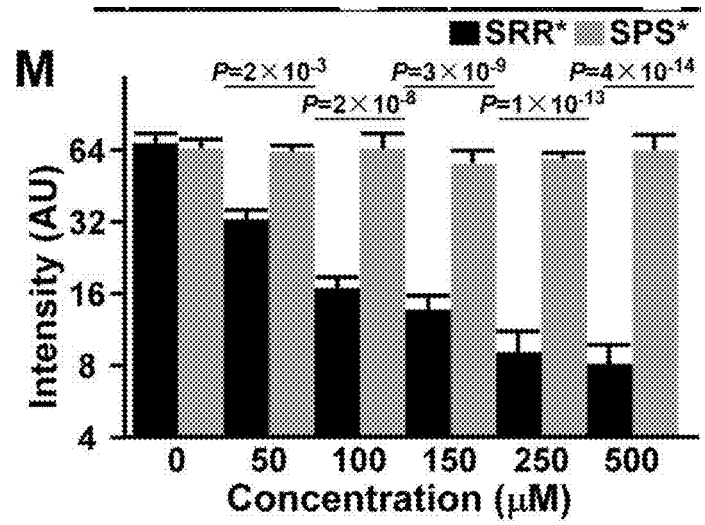
FIG. 3 A-L) shows on competition with addition of unlabeled SRR* peptide at concentrations of 50 µM and higher, we observed a significant decrease in binding of SRR*-Cy5.5 to QhTERT cells that express FGFR2c. G-L) Non-significant differences were found with the addition of unlabeled SPS*.
Figure 3:
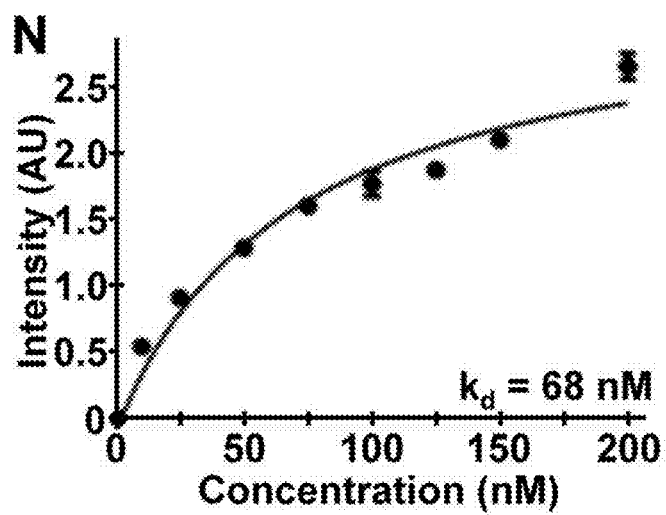
Figure 3:
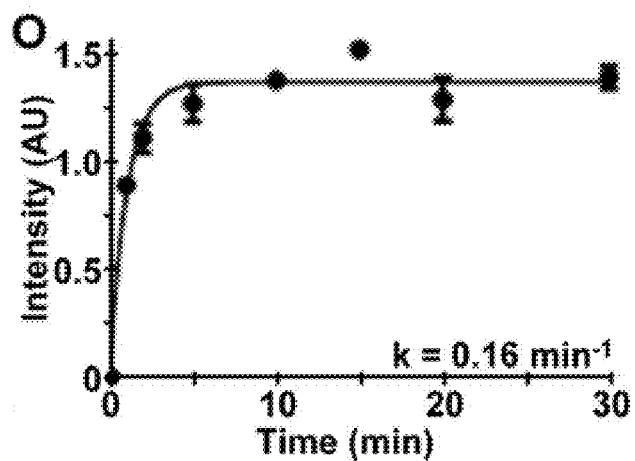
Figure 3:
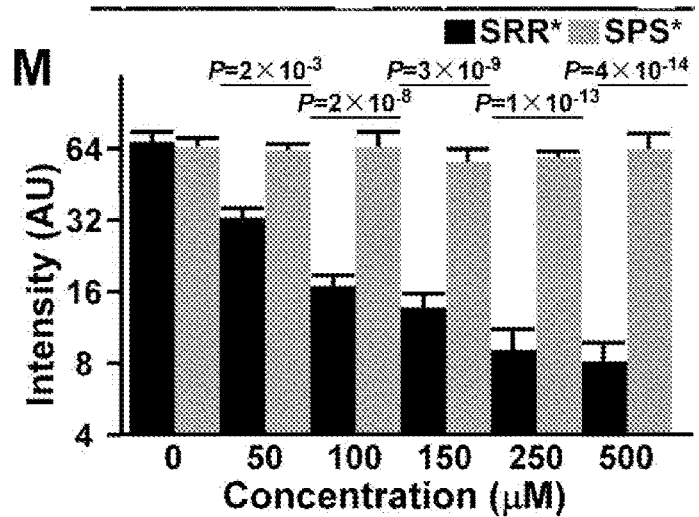
Figure 3:
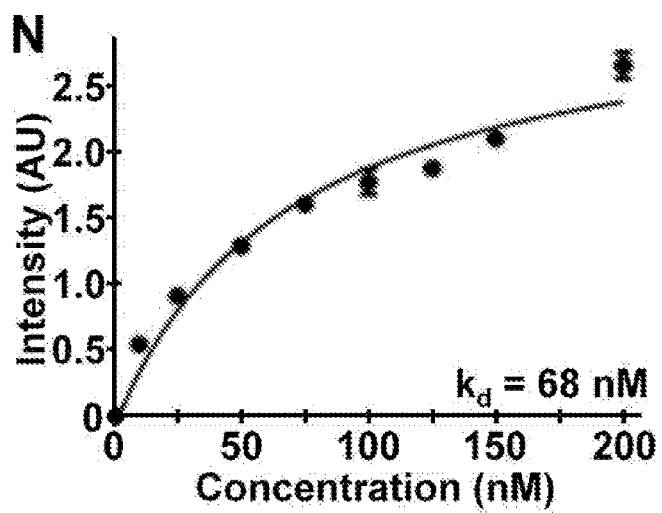
Figure 3:
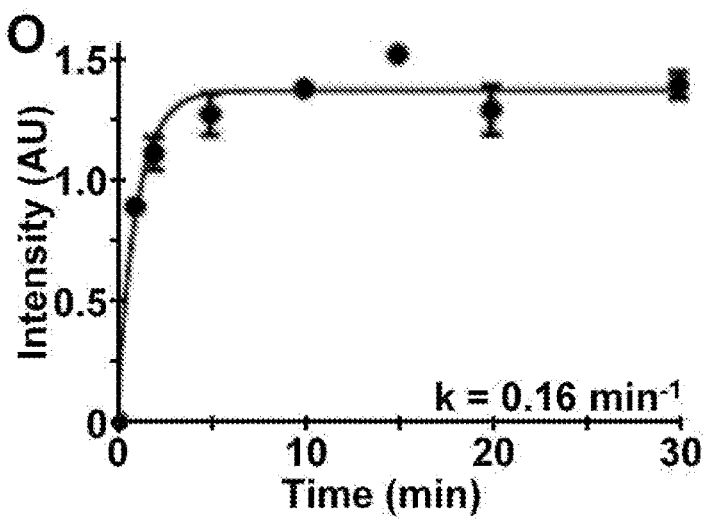

We quantified the mean fluorescence intensities, and observed a significant reduction at concentrations of 50 µM and greater of SRR* compared with that at 0 µM, FIG. 3M. No significant difference was found with addition of unlabeled control SPS* at any concentration. This result supports binding of the peptide component of the reagent rather than the fluorophore component to FGFR2.

Example 5

Characterization of Peptide Reagent Binding Affinity

We measured the apparent dissociation constant $k_d$ for peptide reagent binding to cells to assess binding affinity.[45] The Cy5.5-labeled peptide reagent was serially diluted in PBS at concentrations ranging from 0 to 200 nM in 25 nM increments. QhTERT/FGFR2c cells (~$10^5$) were incubated with peptide at 4° C. for 1 hour, washed with cold PBS, and the mean fluorescence intensities were measured using flow cytometry. The equilibrium dissociation constant $k_d=1/k_a$ was calculated by performing a least squares fit of the data to the non-linear equation $I=(I_0+I_{max}k_a[X])/(I_0+k_a[X])$. $I_0$ and $I_{max}$ are the initial and maximum fluorescence intensities, corresponding to no peptide and at saturation, respectively, and [X] represents the concentration of the bound peptide reagent. Prism 5.0 software (GraphPad Inc) was used to calculate $k_d$.

We measured the apparent association time constant of the peptide reagent to QhTERT/FGFR2c cells to assess binding onset.[46] Cells were grown to ~80% confluence in 10 cm dishes, and detached with PBS-based cell dissociation buffer (Invitrogen). Cells (~$10^5$) were incubated with 5 μM SRR*-Cy5.5 at RT for various time intervals ranging from 0 to 30 min. The cells were centrifuged, and washed with cold PBS. Flow cytometry analysis was performed as described above, and the median fluorescence intensity (y) were measured on flow cytometry at different time points (t) using Flowjo software. The rate constant k was calculated by fitting the data to a first order kinetics model, $y(t)=I_{max}[1-\exp^{(-kt)}]$, where $I_{max}$=maximum value using Prism 5.0 software (GraphPad Inc).

We observed an apparent dissociation constant of $k_d$=68 nM for binding of SRR*-Cy5.5 to QhTERT cells that express FGFR2c, FIG. 3N. This result provides an estimate for binding affinity. We also measured an apparent association time constant of k=0.16 $min^{-1}$ for binding of SRR*-Cy5.5 to QhTERT cells that express FGFR2c, FIG. 3O. This result provides time scale of ~6.2 min for onset of binding.

Example 6

Binding of FGFR2 Peptide Reagent and Antibody to Human Esophageal Specimens.

On confocal microscopy, we evaluated staining of the FGFR2 peptide reagent SRR*-Cy5.5 to sections of human esophagus ex vivo.

Formalin-fixed sections of human esophageal specimens were deparaffinized, and antigen retrieval was performed using standard methods. Briefly, the sections were incubated in xylene for 3 min 3×, washed with 100% ethanol for 2 min 2×, and washed with 95% ethanol for 2 min 2×. Rehydration was performed by washing in $dH_2O$ for 5 min 2×. Antigen unmasking was performed by boiling the slides in 10 mM sodium citrate buffer with 0.05% Tween at pH 6.0, and then maintaining at sub-boiling temperature for 15 min. The slides were cooled for 30 min, and the sections were washed in $dH_2O$ for 3 min 3× and in PBS for 5 min. Blocking was performed with DAKO protein blocking agent (X0909, DAKO) for 1 hour at RT. The peptides were incubated at a concentration of 1 μM for 10 min at RT. The sections were washed in PBS for 3 min 3×, and incubated with 1:1000 dilution of monoclonal anti-FGFR2 (Abcam, ab58201) overnight at 4° C.

The sections were then washed in PBS for 5 min 3×. A 1:500 dilution of AF488-labeled secondary antibody (goat anti-mouse) was added to each section and incubated for 30 min at RT. The secondary antibody solution was removed by washing with PBS for 5 min 3×. The sections were then mounted with ProLong Gold reagent containing DAPI (Invitrogen). The mean fluorescence intensities from 3 boxes (dimensions of 30×30 $m^2$) located completely within the surface epithelium of each specimen were measured. Regions that showed intensity saturation were avoided. Serial sections were processed for routine histology (H&E), and were reviewed by an expert gastrointestinal pathologist (HDA).

Figure 4:
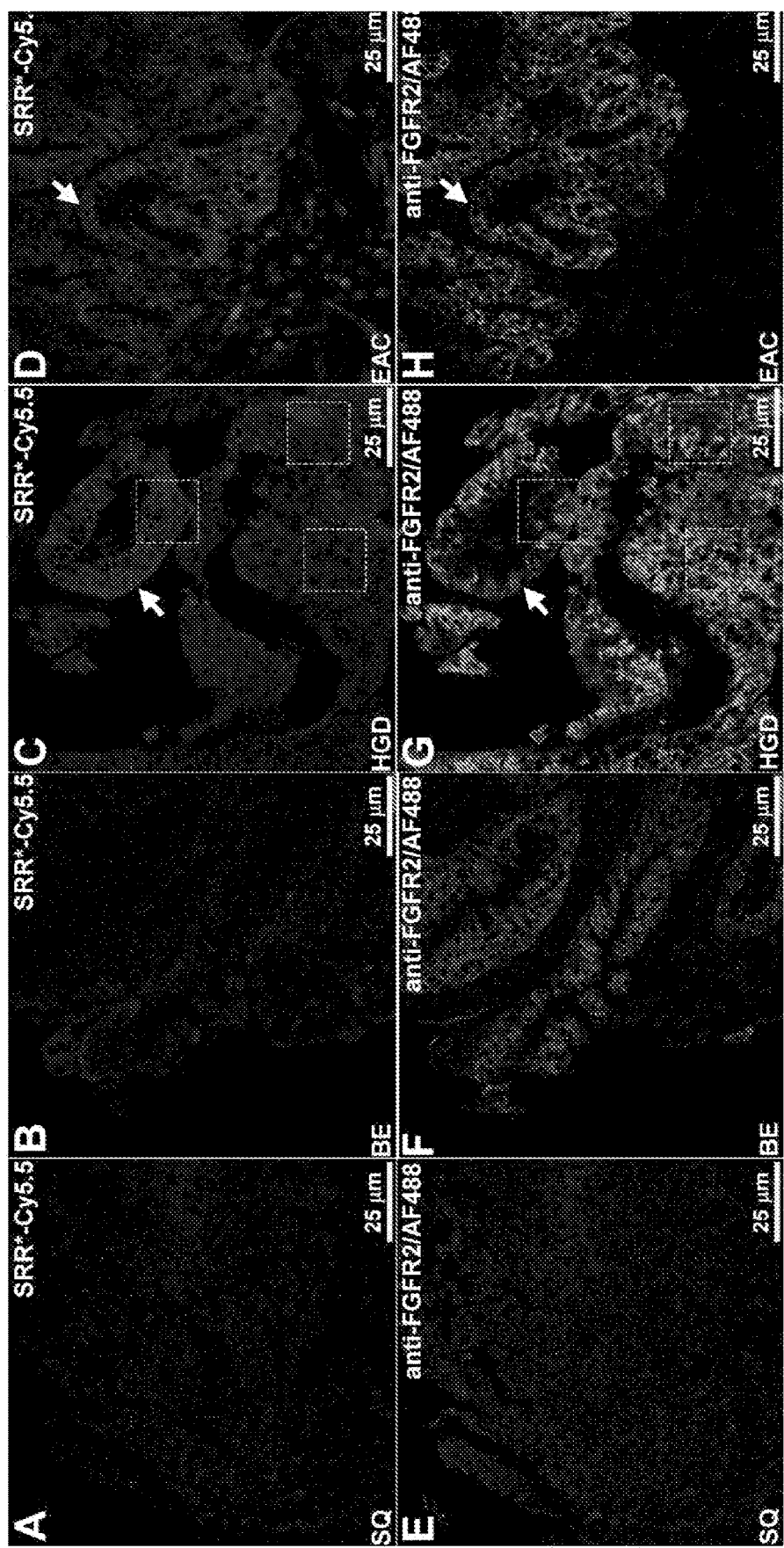
FIG. 4 shows on representative images collected with confocal microscopy of human esophageal specimens ex vivo, SRR*-Cy5.5 (red) shows minimal staining to A) squamous (SQ) and B) Barrett's esophagus (BE) and strong binding (arrows) to C) high-grade dysplasia (HGD) and D) esophageal adenocarcinoma (EAC). E-H) Anti-FGFR2 antibody labeled with AF488 (green) was used as a positive control, and shows weak staining to SQ and BE but strong binding (arrows) to HGD and EAC. We quantified the fluorescence intensities from the mean of a set of 3 boxes with dimensions of 30×30 µm$^2$ placed over cells, shown in panels C) and G). From n=28, 33, 22, and 17 specimens of SQ, BE, HGD, and EAC, respectively, we found significantly greater mean fluorescence intensity from HGD and EAC compared with that for BE with I) SRR*-Cy5.5 and J) AF488-labeled anti-FGFR2 using an ANOVA model with terms for 4 means on log-transformed data. K-N) Merged images shows co-localization of peptide (red) and antibody (green) binding. We determined a Pearson's correlation coefficient of p=0.59, 0.54, 0.52 and 0.59 for SQ, BE, HGD and EAC, respectively. Representative histology (H&E) are shown for O) SQ, P) BE, Q) HGD, and R) EAC.
Figure 4:
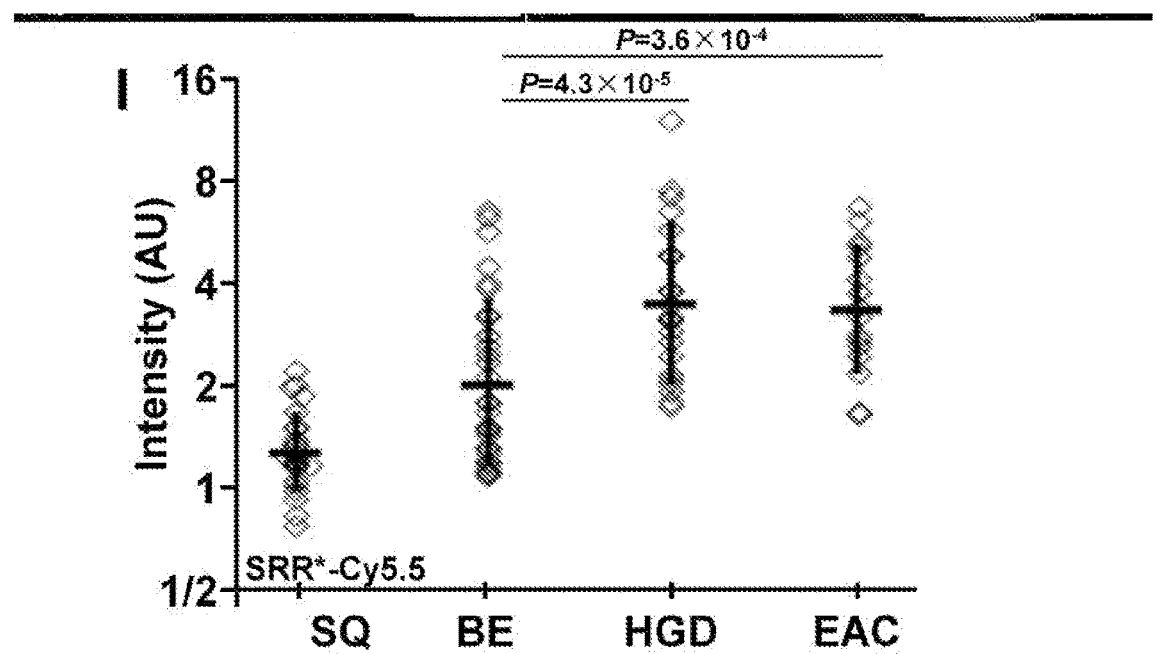
Figure 4:
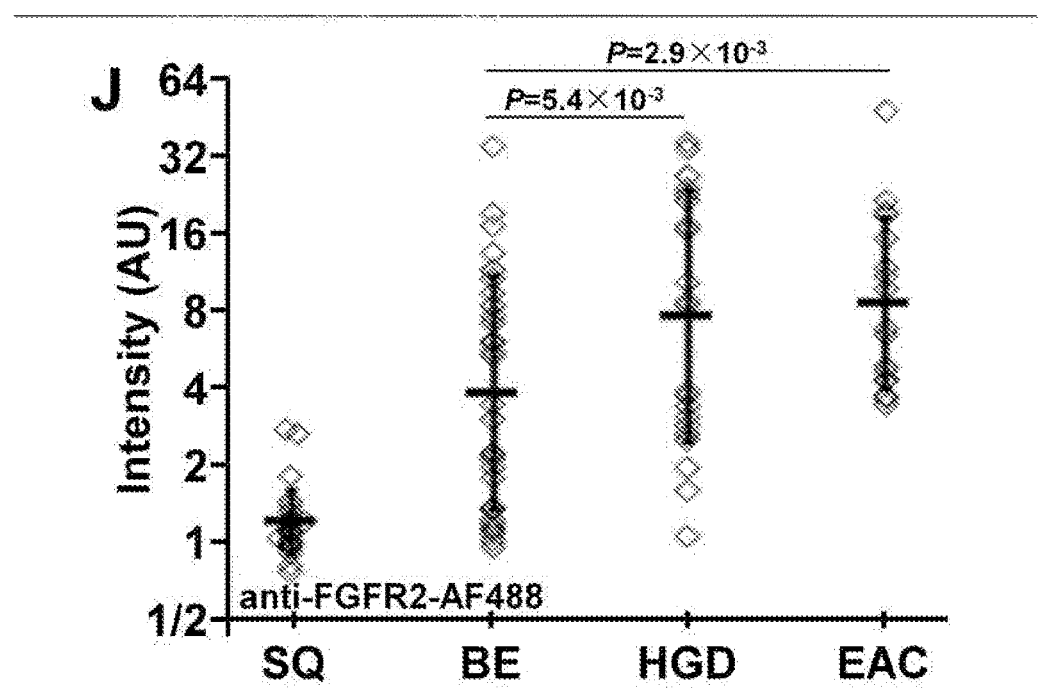
Figure 4:
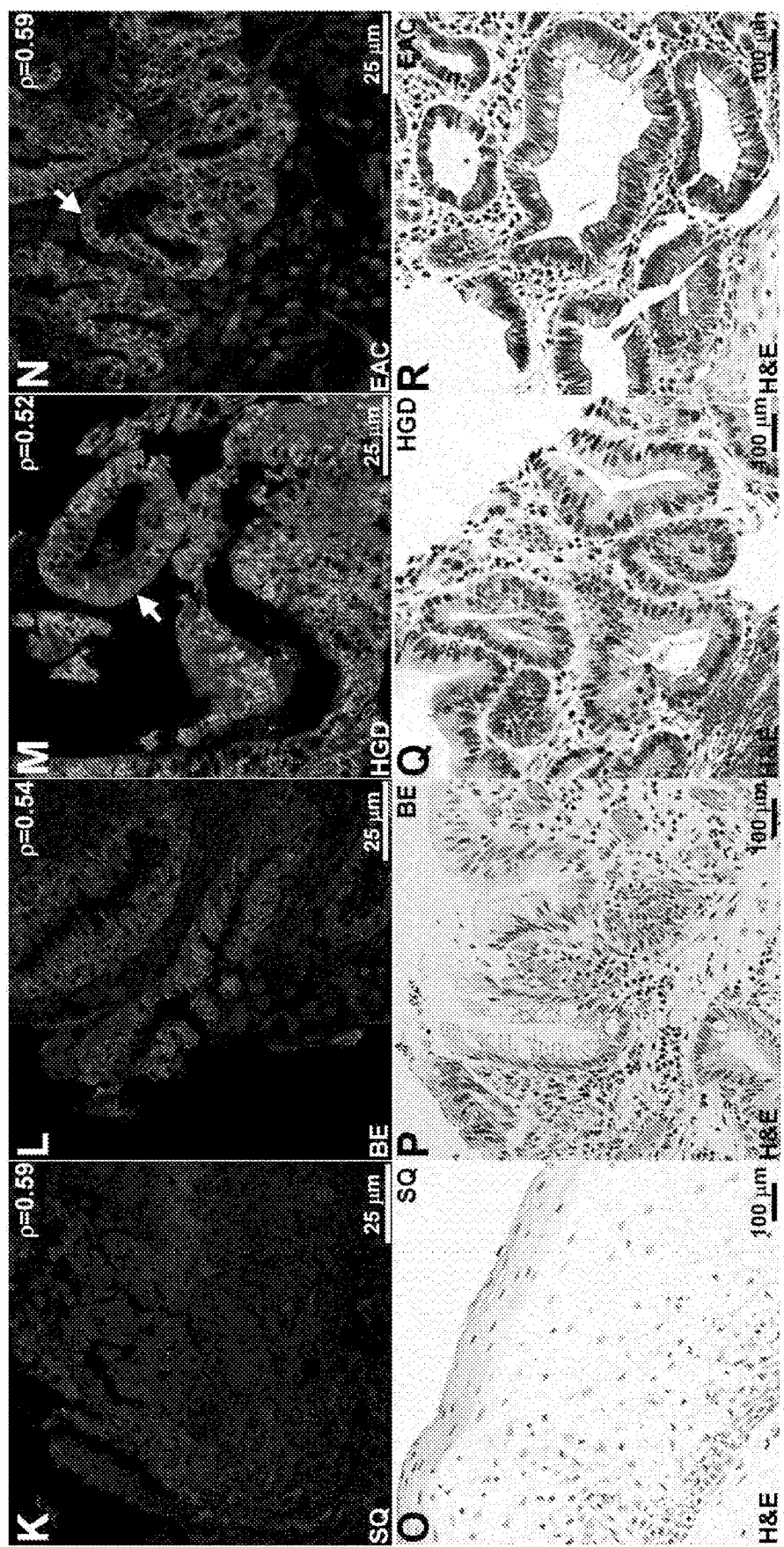

We observed minimal fluorescence intensity with squamous (SQ) and BE, FIG. 4A,B, and strong signal with HGD and EAC, FIG. 4C,D. We confirmed these results with AF488-labeled anti-FGFR2 antibody, FIG. 4E-H. Fluorescence intensities were measured from a set of 3 boxes with dimensions of 30×30 $μm^2$ to calculate the target-to-background (T/B) ratio. The mean (±std) T/B ratio for SRR*-Cy5.5 was significantly higher for HGD and EAC than that for BE and SQ, FIG. 4I. These results are consistent with that with control anti-FGFR2 antibody, FIG. 4J. We plot the fluorescence intensities for all specimens, and found good correlation between SRR*-Cy5.5 and anti-FGFR2-AF488 with R=0.66, FIG. 9. Co-localization of peptide reagent and antibody binding can be seen on merged images, FIG. 4K-N. Corresponding histology (H&E) were shown in FIG. 4O-R.

Example 7

Binding of FGFR2 Peptide to Human Squamous Cell and Gastric Cancer

On confocal microscopy, we observed strong fluorescence intensity from staining of the FGFR2 peptide reagent SRR*-Cy5.5 to sections of human esophageal squamous cell cancer (SCC) ex vivo in n=35 patients, FIG. 10A. We confirmed this result with AF488-labeled anti-FGFR2 antibody, FIG. 10B. We observed good co-localization of peptide reagent and antibody binding on merged images, FIG. 10C. Representative histology (H&E) for SCC is shown, FIG. 10D. By comparison, we observed minimal fluorescence intensity in normal human esophagus with either peptide reagent or antibody, FIG. 10E-G. Representative histology (H&E) for normal stomach is shown, FIG. 10H.

On confocal microscopy, we also observed strong fluorescence intensity from staining of the FGFR2 peptide reagent SRR*-Cy5.5 to sections of human gastric cancer ex vivo in n=33 patients, FIG. 11A. We confirmed this result with AF488-labeled anti-FGFR2 antibody, FIG. 11B. We observed good co-localization of peptide and antibody binding on merged images, FIG. 11C. Representative histology (H&E) for gastric cancer is shown, FIG. S6D. By comparison, we observed minimal fluorescence intensity in normal human stomach with either peptide or antibody, FIG. S6E-G. Representative histology (H&E) for normal stomach is shown, FIG. 11H.

We quantified fluorescence intensities from a set of 3 boxes with dimensions of 30×30 $μm^2$ in each image and found a significantly greater result for SCC versus normal and for gastric cancer versus normal, FIG. 11I,J, respectively.

Example 8

Effect of Peptide on Cell Signaling

We evaluated the effect of peptide reagent binding on downstream signaling in QhTERT cells that express either FGFR2b or FGFR2c.

QhTERT cells that overexpress either FGFR2b or FGFR2c were seeded in 12-well flat-bottom plates with 500 μL of serum-free medium for 16 hours. FGF1 (#2232-FA-025, R&D systems) was reconstituted to a concentration of 100 μg/mL using PBS, diluted with 0.1% bovine serum albumin, and added to the cells at final concentrations of 100 ng/mL for 20 min in separate wells. Heparin (#H3149-10KU, Sigma) with final concentration of 100 unit/mL was also added to increase stability. In addition, peptides at concentrations of 5 and 100 μM were incubated for 20 min in separate wells. The cells were washed with PBS and lysed in RIPA buffer containing protease inhibitors (#11836170001, Roche, Basel, Switzerland). Lysates were separated by gel electrophoresis, transferred to polyvinylidene difluoride membranes (#ISEQ00010, Millipore), and detected by immunoblotting using an enhanced chemiluminescence system (#RPN2106, GE Healthcare). Anti-FGFR2 antibody (#SC 122, Santa Cruz Biotechnology), anti-phospho-FGFR (#3471, Cell Signaling Technology), anti-AKT (#4691P, Cell Signaling Technology), anti-ERK1/2 (#4695P, Cell Signaling Technology), anti-phospho-AKT (pS473; #4060P, Cell Signaling Technology), anti-phospho-ERK1/2 (#4370P, Cell Signaling Technology), and anti-tubulin (#32-2600, Invitrogen) were used as per manufacturer's instructions.

Figure 5:
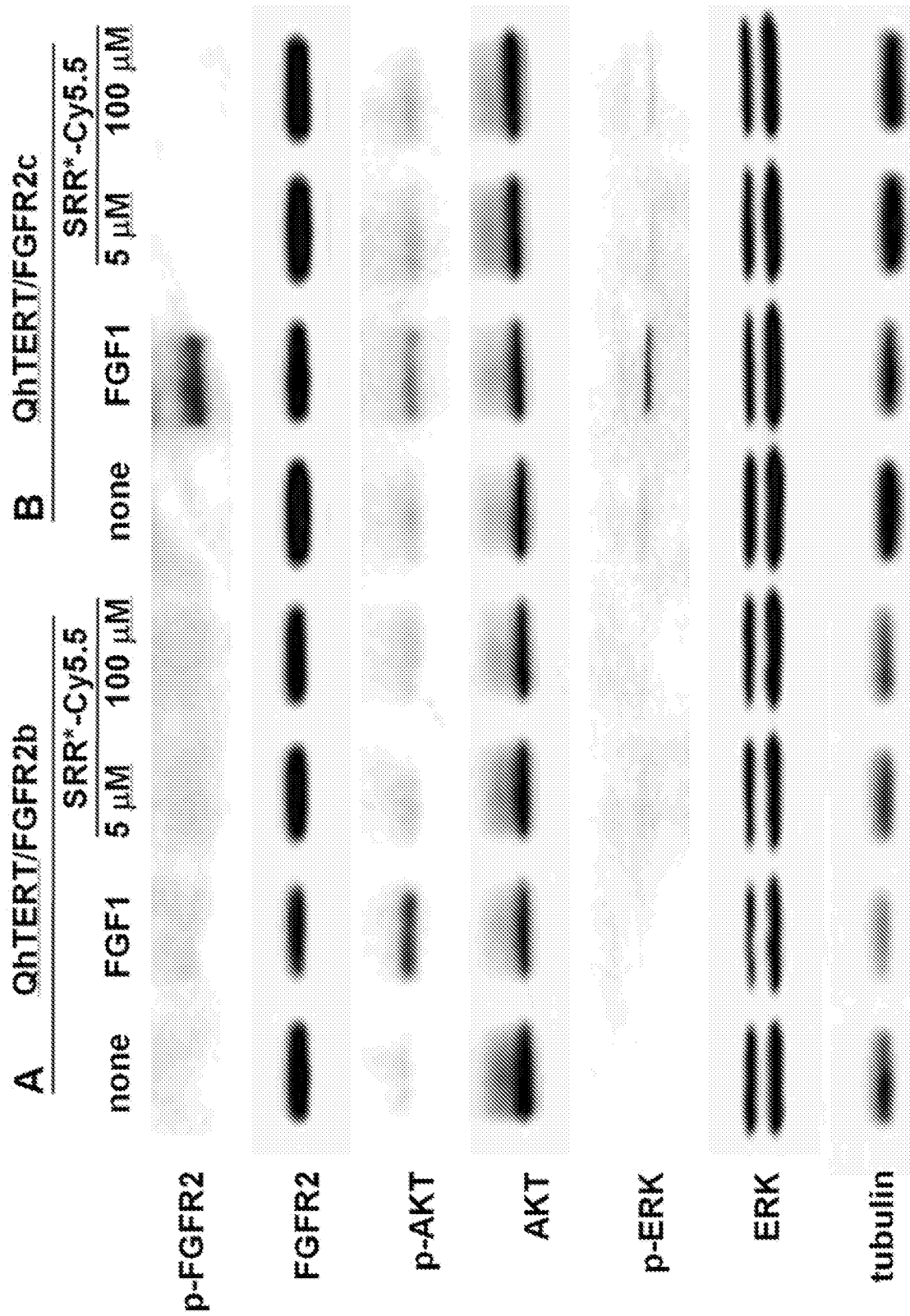
FIG. 5 shows on Western blot no obvious change in phosphorylation for either FGFR2 (p-FGFR) or downstream AKT (p-AKT) and ERK (p-ERK) with addition of SRR* peptide at 5 and 100 µM to QhTERT cells that express FGFR2b or FGFR2c compared with untreated cells. Addition of FGF1 as positive control to bind FGFR2b and FGFR2c shows phosphorylation activity for FGFR2

Western blot showed no change in phosphorylation of either FGFR2 (p-FGFR) or downstream AKT (p-AKT) and ERK (p-ERK) with addition of SRR* peptide at a concentration of either 5 or 100 μM, FIG. 5A. By comparison, we observed strong phosphorylation activity of FGFR2 (p-FGFR), downstream AKT (p-AKT) and ERK (p-ERK) with addition of positive control FGF1 in QhTERT cells that express FGFR2c and to some extent or FGFR2b.

Example 9

Discussion

Herein, we have identified a novel peptide specific for FGFR2 that binds to the extra-cellular Ig-like domain of isoforms IIIb and IIIc. Expression of FGFR2 has been identified as an early event in progression from BE to EAC.[10] We demonstrate accessibility for imaging by showing that this peptide binds to the cell membrane in vitro, and confirm specificity for FGFR2 using competition results. These studies were rigorously controlled using a scrambled peptide. We found this peptide to bind cells with high affinity of $k_d$=68 nM and rapid binding onset of k=0.16 min$^1$ (6.2 min). We labeled this peptide with Cy5.5, a NIR fluorophore, and visualized specific cell surface staining to neoplasia in human specimens of BE, SCC, and gastric cancer ex vivo. In addition to Barrett's neoplasia, FGFR2 is overexpressed in other epithelial-derived cancers, including esophageal SCC,[38] gastric,[39] esophagogastric junction,[40] colorectal,[41] pancreatic,[42] and breast.[43] We present immunofluorescence results to support broad use of this FGFR2 peptide reagent for detection of esophageal SCC and gastric cancer, FIG. 10, FIG. 11. Thus, we contemplate use of this peptide reagent for clinical imaging in patients at high risk for epithelial-derived cancers in the esophagus and stomach.

We have also identified peptides specific for EGFR and ErbB2.[27,28] These genes are high frequency amplified in EAC.[29] We contemplate using a panel of targets for early detection of Barrett's neoplasia.[10] Peptides have similar binding onsets, and multiplexed detection has been demonstrated in vivo.[21]

We also provide evidence that peptide binding does not affect downstream cell signaling. Therefore, we also contemplate use of this peptide reagent in therapy for labelling nanocarriers. Nanocarriers can be used to achieve site-specific drug delivery of high payloads.[25].

While the present invention has been described in terms of specific embodiments, it is understood that variations and modifications will occur to those skilled in the art. Accordingly, only such limitations as appear in the claims should be placed on the invention.

DOCUMENTS

All documents cited in this application are hereby incorporated by reference in their entirety, with particular attention to the disclosure for which they are referred.
1. Torre L A, Siegel R L, Ward E M, Jemal A. Global Cancer Incidence and Mortality Rates and Trends—An Update. Cancer Epidemiol Biomarkers Prev 2016; 25:16-27.
2. Hur C, Miller M, Kong C Y, Dowling E C, Nattinger K J, Dunn M, Feuer E J. Trends in esophageal adenocarcinoma incidence and mortality. Cancer 2013; 119:1149-58.
3. Whiteman D C, Sadeghi S, Pandeya N, Smithers B M, Gotley D C, Bain C J, Webb P M, Green A C; Australian Cancer Study. Combined effects of obesity, acid reflux and smoking on the risk of adenocarcinomas of the oesophagus. Gut 2008; 57:173-80.
4. Odze R D. Diagnosis and grading of dysplasia in Barrett's oesophagus. J Clin Pathol 2006; 59:1029-38.
5. Curvers W L, ten Kate F J, Krishnadath K K, Visser M, Elzer B, Baak L C, Bohmer C, Mallant-Hent R C, van Oijen A, Naber A H, Scholten P, Busch O R, Blaauwgeers H G, Meijer G A, Bergman J J. Low-grade dysplasia in Barrett's esophagus: overdiagnosed and underestimated. Am J Gastroenterol 2010; 105:1523-30.
6. Wang K K, Sampliner R E; Practice Parameters Committee of the American College of Gastroenterology. Updated guidelines 2008 for the diagnosis, surveillance and therapy of Barrett's esophagus. Am J Gastroenterol 2008; 103:788-97.
7. Sharma P, Savides T J, Canto M I, Corley D A, Falk G W, Goldblum J R, Wang K K, Wallace M B, Wolfsen H C; ASGE Technology and Standards of Practice Committee. The American Society for Gastrointestinal Endoscopy PIVI (Preservation and Incorporation of Valuable Endoscopic Innovations) on imaging in Barrett's Esophagus. Gastrointest Endosc 2012; 76:252-4.
8, Sturm M B, Wang T D. Emerging optical methods for surveillance of Barrett's oesophagus. Gut 2015; 64:1816-23.
9. Sergina N V, Rausch M, Wang D, Blair J, Hann B, Shokat K M, Moasser M M. Escape from HER-family tyrosine kinase inhibitor therapy by the kinase-inactive HER3. Nature 2007; 445:437-41.
10. Paterson A L, O'Donovan M, Provenzano E, Murray L J, Coleman H G, Johnson B T, McManus D T, Novelli M, Lovat L B, Fitzgerald R C. Characterization of the timing and prevalence of receptor tyrosine kinase expression changes in oesophageal carcinogenesis. J Pathol 2013; 230:118-28.
11. Ornitz D M, Itoh N. The Fibroblast Growth Factor signaling pathway. Wiley Interdiscip Rev Dev Biol 2015; 4:215-66.
12. Ibrahimi O A, Eliseenkova A V, Plotnikov A N, Yu K, Ornitz D M, Mohammadi M. Structural basis for fibroblast growth factor receptor 2 activation in Apert syndrome. Proc Natl Acad Sci 2001; 98:7182-7.
13. Orr-Urtreger A, Bedford M T, Burakova T, Arman E, Zimmer Y, Yayon A, Givol D, Lonai P. Developmental localization of the splicing alternatives of fibroblast growth factor receptor-2 (FGFR2). Dev Biol 1993; 158: 475-86.
14. Eswarakumar V P, Lax I, Schlessinger J. Cellular signaling by fibroblast growth factor receptors. Cytokine Growth Factor Rev 2005; 16:139-49.
15. Fletcher M N, Castro M A, Wang X, de Santiago I, O'Reilly M, Chin S F, Rueda O M, Caldas C, Ponder B A, Markowetz F, Meyer K B. Master regulators of FGFR2 signalling and breast cancer risk. Nat Commun 2013; 4:2464-1-12.
16. Dufour C, Guenou H, Kaabeche K, Bouvard D, Sanjay A, Marie P J. FGFR2-Cbl interaction in lipid rafts triggers attenuation of PI3K/Akt signaling and osteoblast survival. Bone 2008; 42:1032-9.
17. Fang X, Yang D, Luo H, Wu S, Dong W, Xiao J, Yuan S, Ni A, Zhang K J, Liu X Y, Chu L. SNORD126 promotes HCC and CRC cell growth by activating the PI3K-AKT pathway through FGFR2. J Mol Cell Biol 2016.
18. Nomura S, Yoshitomi H, Takano S, Shida T, Kobayashi S, Ohtsuka M, Kimura F, Shimizu H, Yoshidome H, Kato A, Miyazaki M. FGF10/FGFR2 signal induces cell migration and invasion in pancreatic cancer. Br J Cancer 2008; 99(2):305-13.
19. Sturm M B, Joshi B P, Lu S, Piraka C, Khondee S, Elmunzer B J, Kwon R S, Beer D G, Appelman H D, Turgeon D K, Wang T D. Targeted imaging of esophageal neoplasia with a fluorescently labeled peptide: first-in-human results. Sci Transl Med 2013; 5:184ra61.
20. Joshi B P, Duan X, Kwon R S, Piraka C, Elmunzer B J, Lu S, Rabinsky E F, Beer D G, Appelman H D, Owens S R, Kuick R, Doguchi N, Turgeon D K, Wang T D. Multimodal endoscope can quantify wide-field fluorescence detection of Barrett's neoplasia. Endoscopy 2016; 48:A1-A13.
21. Joshi B P, Miller S J, Lee C M, Seibel E J, Wang T D. Multispectral endoscopic imaging of colorectal dysplasia in vivo. Gastroenterology 2012; 143:1435-7.
22. Sturm M B, Piraka C, Elmunzer B J, Kwon R S, Joshi B P, Appelman H D, Turgeon D K, Wang T D. In vivo molecular imaging of Barrett's esophagus with confocal laser endomicroscopy. Gastroenterology 2013; 145:56-8.
23. Luo S, Zhang E, Su Y, Cheng T, Shi C. A review of NIR dyes in cancer targeting and imaging. Biomaterials 2011; 32:7127-38.
24. Plotnikov A N, Hubbard S R, Schlessinger J, Mohammadi M. Crystal structures of two FGF-FGFR complexes reveal the determinants of ligand-receptor specificity. Cell 2000; 101:413-24.
25. Khondee S, Rabinsky E F, Owens S R, Joshi B P, Qiu Z, Duan X, Zhao L, Wang T D. Targeted therapy of colorectal neoplasia with rapamycin encapsulated in peptide-labeled pegylated octadecyl lithocholate micelles, J Control Release 2015; 199:114-21.
26. Boonstra J J, van Marion R, Beer D G, Lin L, Chaves P, Ribeiro C, Pereira A D, Roque L, Darnton S J, Altorki N K, Schrump D S, Klimstra D S, Tang L H, Eshleman J R, Alvarez H, Shimada Y, van Dekken H, Tilanus H W, Dinjens W N. Verification and unmasking of widely used human esophageal adenocarcinoma cell lines. J Natl Cancer Inst 2010; 102:271-4.
27. Zhou J, Joshi B P, Duan X, Pant A, Qiu Z, Kuick R, Owens S R, Wang T D. EGFR Overexpressed in Colonic Neoplasia Can be Detected on Wide-Field Endoscopic Imaging. Clin Transl Gastroenterol. 2015 Jul. 16; 6:e101.
28. Joshi B P, Zhou J, Pant A, Duan X, Zhou Q, Kuick R, Owens S R, Appelman H, Wang T D. Design and Synthesis of Near-Infrared Peptide for in Vivo Molecular Imaging of HER2. Bioconjug Chem 2016; 27:481-94.
29. Dulak A M, Stojanov P, Peng S, Lawrence M S, Fox C, Stewart C, Bandla S, Imamura Y, Schumacher S E, Shefler E, McKenna A, Carter S L, Cibulskis K, Sivachenko A, Saksena G, Voet D, Ramos A H, Auclair D, Thompson K, Sougnez C, Onofrio R C, Guiducci C, Beroukhim R, Zhou Z, Lin L, Lin J, Reddy R, Chang A, Landrenau R, Pennathur A, Ogino S, Luketich J D, Golub T R, Gabriel S B, Lander E S, Beer D G, Godfrey T E, Getz G, Bass A J. Exome and whole-genome sequencing of esophageal adenocarcinoma identifies recurrent driver events and mutational complexity. Nat Genet 2013; 45:478-86.
30. Bi F, Yin H, Zheng S, Zhu Q, Yang H, Kang M, Gan F, Chen X. One-step synthesis of peptide conjugated gold nanoclusters for the high expression of FGFR2 tumor targeting and imaging. RSC Adv 2016; 6:4627-33.
31. Bai A, Meetze K, Vo N Y, Kollipara S, Mazsa E K, Winston W M, Weiler S, Poling L L, Chen T, Ismail N S, Jiang J, Lerner L, Gyuris J, Weng Z. GP369, an FGFR2-IIIb-specific antibody, exhibits potent antitumor activity against human cancers driven by activated FGFR2 signaling. Cancer Res 2010; 70:7630-9.
32. Wu A M, Senter P D. Arming antibodies: prospects and challenges for immunoconjugates. Nat Biotechnol 2005; 23:1137-46.
33. Bird-Lieberman E L, Neves A A, Lao-Sirieix P, O'Donovan M, Novelli M, Lovat L B, Eng W S, Mahal L K, Brindle K M, Fitzgerald R C. Molecular imaging using fluorescent lectins permits rapid endoscopic identification of dysplasia in Barrett's esophagus. Nat Med 2012; 18:315-21.
34. Kim S T, Jang H L, Lee S J, Lee J, Choi Y L, Kim K M, Cho J, Park S H, Park Y S, Lim H Y, Yashiro M, Kang W K, Park J O. Pazopanib, a novel multitargeted kinase inhibitor, shows potent in vitro antitumor activity in gastric cancer cell lines with FGFR2 amplification. Mol Cancer Ther 2014; 13:2527-36.
35. Ngamruengphong S, Sharma V K, Das A. Diagnostic yield of methylene blue chromoendoscopy for detecting specialized intestinal metaplasia and dysplasia in Barrett's esophagus: a meta-analysis. Gastrointest Endosc 2009; 69:1021-8.
36. Mannath J, Subramanian V, Hawkey C J, Ragunath K. Narrow band imaging for characterization of high grade dysplasia and specialized intestinal metaplasia in Barrett's esophagus: a meta-analysis. Endoscopy 2010; 42:351-9.
37. Giacchino M, Bansal A, Kim R E, Singh V, Hall S B, Singh M, Rastogi A, Moloney B, Wani S B, Gaddam S, Mathur S C, Wallace M B, Kanakadandi V, Balasubramanian G, Gupta N, Sharma P. Clinical utility and interobserver agreement of autofluorescence imaging and magnification narrow-band imaging for the evaluation of Barrett's esophagus: a prospective tandem study. Gastrointest Endosc 2013; 77:711-8.
38. Kato H, Arao T, Matsumoto K, Fujita Y, Kimura H, Hayashi H, Nishiki K, Iwama M, Shiraishi O, Yasuda A, Shinkai M, Imano M, Imamoto H, Yasuda T, Okuno K, Shiozaki H, Nishio K. Gene amplification of EGFR, HER2, FGFR2 and MET in esophageal squamous cell carcinoma. Int J Oncol 2013; 42:1151-8.
39. Han N, Kim M A, Lee H S, Kim W H. Evaluation of Fibroblast Growth Factor Receptor 2 Expression, Heterogeneity and Clinical Significance in Gastric Cancer. Pathobiology 2015; 82:269-79.
40. Tokunaga R, Imamura Y, Nakamura K, Ishimoto T, Nakagawa S, Miyake K, Nakaji Y, Tsuda Y, Iwatsuki M, Baba Y, Sakamoto Y, Miyamoto Y, Saeki H, Yoshida N, Oki E, Watanabe M, Oda Y, Bass A J, Maehara Y, Baba H. Fibroblast growth factor receptor 2 expression, but not its genetic amplification, is associated with tumor growth and worse survival in esophagogastric junction adenocarcinoma. Oncotarget 2016; 7:19748-61.
41. Matsuda Y, Ueda J, Ishiwata T. Fibroblast growth factor receptor 2: expression, roles, and potential as a novel molecular target for colorectal cancer. Patholog Res Int 2012; 2012:574768.
42. Matsuda Y, Yoshimura H, Suzuki T, Uchida E, Naito Z, Ishiwata T. Inhibition of fibroblast growth factor receptor 2 attenuates proliferation and invasion of pancreatic cancer. Cancer Sci 2014; 105:1212-9.

43. Lee H J, Seo A N, Park S Y, Kim J Y, Park J Y, Yu J H, Ahn J H, Gong G. Low prognostic implication of fibroblast growth factor family activation in triple-negative breast cancer subsets. Ann Surg Oncol 2014; 21:1561-8.
44. Merrifield R B. Solid Phase Peptide Synthesis. I. The Synthesis of a Tetrapeptide. J Am Chem Soc 1963; 85:2149-2154.
45. Thomas R, Chen J, Roudier M M, Vessella R L, Lantry L E, Nunn A D. In vitro binding evaluation of 177Lu-AMBA, a novel 177Lu-labeled GRP-R agonist for systemic radiotherapy in human tissues. Clin Exp Metastasis. 2009; 26:105-19. PMID: 18975117.
46. Joshi B P, Liu Z, Elahi S F, Appelman H D, Wang T D. Near-infrared-labeled peptide multimer functions as phage-mimic for high affinity, specific targeting of colonic adenomas in vivo, Gastrointestinal Endoscopy 2012; 2012; 76:1197-206. PMID: 23022051.

We claim:

1. A reagent comprising a fibroblast growth factor receptor 2-specific peptide SRRPASFRTARE (SEQ ID NO: 1), or a multimer form of the peptide,
   wherein the peptide specifically binds to fibroblast growth factor receptor 2 and
   wherein at least one detectable label, at least one therapeutic moiety, or both, are attached to the peptide or a multimer form of the peptide.

2. The reagent of claim 1 comprising at least one detectable label attached to the peptide.

3. The reagent of claim 2 wherein the detectable label is detectable by optical, photoacoustic, ultrasound, positron emission tomography or magnetic resonance imaging.

4. The reagent of claim 3 wherein the label detectable by optical imaging is fluorescein isothiocyanate (FITC), Cys, Cy5.5 or IRdye800.

```
                          SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Ser Arg Arg Pro Ala Ser Phe Arg Thr Ala Arg Glu
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic Linker

<400> SEQUENCE: 2

Gly Gly Gly Ser Lys
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 3

Gly Leu His Thr Ser Ala Thr Asn Leu Tyr Leu His
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Ala Ser Tyr Asn Tyr Asp Ala
1               5
```

5. The reagent of claim 1 wherein the multimer form of the peptide is a dimer formed with an aminohexanoic acid linker.

6. The reagent of claim 2 wherein the detectable label is attached to the peptide by a peptide linker.

7. The reagent of claim 6 wherein a terminal amino acid of the linker is lysine.

8. The reagent of claim 7 wherein the linker comprises the sequence GGGSK set out in SEQ ID NO: 2.

9. The reagent of 1 comprising at least one therapeutic moiety attached to the peptide.

10. The reagent of claim 9 wherein the therapeutic moiety is chemotherapeutic agent.

11. The reagent of claim 9 wherein the therapeutic moiety is a polymeric nanoparticle or micelle.

12. The reagent of claim 10 wherein the micelle is an octadecyl lithocholate micelle.

13. The reagent of claim 12 wherein the nanoparticle or micelle is pegylated.

14. The reagent of claim 10 wherein the nanoparticle or micelle encapsulates carboplatin, paclitaxel, cisplatin, 5-fluorouracil (5-FU), oxaliplatin, capecitabine, irinotecan chlorambucil or sorafenib.

15. A composition comprising the reagent of claim 1 and a pharmaceutically acceptable excipient.

16. A method for detecting epithelial-derived cancer cells in a patient comprising the steps of administering the reagent of claim 1 to the patient and detecting binding of the reagent to epithelial-derived cancer cells.

17. A method of determining the effectiveness of a treatment for epithelial-derived cancer in a patient comprising the step of administering the reagent of claim 1 to the patient, visualizing a first amount of epithelial-derived cancer cells labeled with the reagent, and comparing the first amount to a previously-visualized second amount of cells labeled with the reagent,
wherein a decrease in the first amount cells labeled relative to the previously-visualized second amount of cells labeled is indicative of effective treatment.

18. The method of claim 14 further comprising obtaining a biopsy of the cells labeled by the reagent.

19. A method for delivering a therapeutic moiety to epithelial-derived cancer cells of a patient comprising the step of administering the reagent of claim 9 to the patient.

20. A kit for administering the composition of claim 15 to a patient in need thereof, said kit comprising the composition of claim 15, instructions for use of the composition and a device for administering the composition to the patient.

21. A peptide consisting of the amino acid sequence SRRPASFRTARE (SEQ ID NO: 1).

* * * * *

UNITED STATES PATENT AND TRADEMARK OFFICE
CERTIFICATE OF CORRECTION

| | |
|---|---|
| PATENT NO. | : 11,406,720 B2 |
| APPLICATION NO. | : 16/625054 |
| DATED | : August 9, 2022 |
| INVENTOR(S) | : Thomas D. Wang et al. |

It is certified that error appears in the above-identified patent and that said Letters Patent is hereby corrected as shown below:

In the Claims

At Column 26, Line 7, "2 and" should be -- 2, and --.

At Column 26, Line 18, "Cys," should be -- Cy5, --.

At Column 27, Line 10, "of 1" should be -- of claim 1 --.

At Column 28, Line 11, "amount cells" should be -- amount of cells --.

At Column 28, Line 14, "method" should be -- reagent --.

Signed and Sealed this
Seventh Day of February, 2023

Katherine Kelly Vidal
*Director of the United States Patent and Trademark Office*